(12) United States Patent
Gerber et al.

(10) Patent No.: US 11,747,345 B2
(45) Date of Patent: Sep. 5, 2023

(54) PREDICTION AND TREATMENT OF IMMUNOTHERAPEUTIC TOXICITY

(71) Applicant: The Board of Regents of the University of Texas System, Austin, TX (US)

(72) Inventors: David E. Gerber, Dallas, TX (US); Edward Wakeland, Dallas, TX (US); Quan Li, Dallas, TX (US); Saad Khan, Dallas, TX (US); Jason Y. Park, Dallas, TX (US); Xin Luo, Dallas, TX (US); Yang Xie, Dallas, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 16/487,335

(22) PCT Filed: Feb. 19, 2018

(86) PCT No.: PCT/US2018/018594
§ 371 (c)(1),
(2) Date: Aug. 20, 2019

(87) PCT Pub. No.: WO2018/156448
PCT Pub. Date: Aug. 30, 2018

(65) Prior Publication Data
US 2020/0284803 A1      Sep. 10, 2020

Related U.S. Application Data

(60) Provisional application No. 62/461,455, filed on Feb. 21, 2017.

(51) Int. Cl.
*G01N 33/68* (2006.01)
*C07K 16/28* (2006.01)

(52) U.S. Cl.
CPC ..... *G01N 33/6854* (2013.01); *C07K 16/2818* (2013.01); *G01N 2800/24* (2013.01)

(58) Field of Classification Search
CPC .......... G01N 2800/24; G01N 2800/52; G01N 33/574
See application file for complete search history.

(56) References Cited

U.S. PATENT DOCUMENTS

2015/0044224 A1 * 2/2015 Soliman ............ G01N 33/574
424/142.1
2015/0118244 A1   4/2015 Shahabi et al.

FOREIGN PATENT DOCUMENTS

WO    WO-2017040464 A1 * 3/2017 ............ A61P 13/12

OTHER PUBLICATIONS

Champiat et al., "Management of immune checkpoint blockade dysimmune toxicities: a collaborative position paper," Annals of Oncology, 27:559-574, 2016. (Year: 2016).*
Kahler et al.Treatment and side effect management of CTLA-4 antibody therapy in metastatic melanoma.JDDG; 2011 • 9:277-285 (Year: 2011).*
Day et al.Immune-Related Adverse Events Associated with Immune Checkpoint Inhibitors. Bio-Drugs (2016) 30:571-584 (Year: 2016).*
Fadel et al. Anti-CTLA4 Antibody-Induced Lupus Nephritis.(New England Journal Medicine 361; 2 Jul. 9, 2009 (Year: 2009).*
Zhu et al.Autoantigen Microarray for High-throughput Autoantibody Profiling in Systemic Lupus ErythematosusGenomics Proteomics Bioinformatics 13 (2015) 210-218 (Year: 2015).*
Olsen et al. Autoantibody profiling to follow evolution of lupus syndromes. (Arthritis Research & Therapy 2012, 14:R174) (Year: 2012).*
Seret et al.Mesangial Cell-Specific Antibodies Are Central to the Pathogenesis of Lupus Nephritis.Clinical and Developmental Immunology vol. 2012, Article ID 579670, 8 pages. 2012 (Year: 2012).*
Baum, "UTSW Medical Center Autoantigen Array," public on Dec. 25, 2014, located at https://www.ncbi.nlm.nih.gov/geo/query/acc.cgi?acc=GPL19451, retrieved from internet Apr. 16, 2018.
Champiat et al., "Management of immune checkpoint blockade dysimmune toxicities: a collaborative position paper," *Annals of Oncology*, 27:559-574, 2016.
Donia et al., "Cancer immunotherapy in patients with preexisting autoimmune disorders," *Semin Immunopathol.*, 39(3):333-337, 2017.
Gelao et al., "Immune checkpoint blockade in cancer treatment: a double-edged sword cross-targeting the host as an 'innocent bystander,'" *Toxins*, 6:914-933, 2014.
Howell et al., "Optimal management of immune-related toxicities associated with checkpoint inhibitors in lung cancer," *Lung Cancer*, 88(2):117-123, 2015.
Khan et al., "Characteristics and Mortality of Patients with Lung Cancer and Autoimmune Disease," Presentation, Eastern Cooperative Oncology Group (ECOG) Young Investigator Symposium, Nov. 2016.
Khan et al., "Immune dysregulation in cancer patients developing immune-related adverse events," *Brit J Cancer*, 120(1):63-68, 2019.
Khan et al., "Prevalence of autoimmune conditions among patients with lung cancer: Implications for immunotherapy treatment options," Annual Meeting of the American Society of Clinical Oncology, *J Clin Oncol.*, 34:suppl abstract 9039, 2016.
Khan et al., "Prevalence of Autoimmune Disease Among Patients With Lung Cancer: Implications for Immunotherapy Treatment Options," *JAMA Oncol.*, 2(11):1507-1508, 2016.
Li et al., "Protein array autoantibody profiles for insights into systemic lupus erythematosus and incomplete lupus syndromes," *Clinical and Experimental Immunology*, 147:60-70, 2006.
Li et al., "Risk factors for ANA positivity in healthy persons," *Arthritis Research & Therapy*, 13:R38, 2011.
Manson et al., "Biomarkers associated with checkpoint inhibitors," *Annals of Oncology*, 27:1199-1206, 2016.

(Continued)

*Primary Examiner* — Amy E Juedes
*Assistant Examiner* — Brian Hartnett
(74) *Attorney, Agent, or Firm* — POLSINELLI PC

(57) ABSTRACT

The present disclosure is directed to methods and compositions for the prediction and treatment of immunotherapy-induced toxicities, as well as improved methods for the treatment of cancer with immunotherapies.

17 Claims, 11 Drawing Sheets

(56) References Cited

OTHER PUBLICATIONS

Michot et al., "Immune-related adverse events with immune checkpoint blockade: a comprehensive review," *European Journal of Cancer*, 54:139-148, 2016.
PCT International Search Report and Written Opinion issued in International Application No. PCT/US2018/018594, dated Jun. 29, 2018.
Postow et al., "Nivolumab and ipilimumab versus ipilimumab in untreated melanoma," *N Engl J Med*, 372(21):2006-2017, 2015.
Raj et al., "Regulatory polymorphisms modulate the expression of HLA class II molecules and promote autoimmunity," *eLife*, 5:e12089, 2016.
Topalian et al., "Safety, activity, and immune correlates of anti-PD-1 antibody in cancer," *N Engl J Med*, 366(26):2443-2454, 2012.
Wandstrat et al., "Autoantibody profiling to identify individuals at risk for systemic lupus erythematosus," *Journal of Autoimmunity*, 27:153-160, 2006.
Leslie, D. et al. "Autoantibodies as predictors of disease," The Journal of Clinical Investigation—Autoimmune diseases, Perspective Series, Nov. 2001, pp. 1417-1422, vol. 108, No. 10, DOI:10.1172/JCI200114452.
Quest Diagonostics, "Tests for Autoimmune Diseases," retrieved from the Internet Dec. 12, 2022 at <https://www.questdiagnostics.com/healthcare-professionals/clinical-education-center/faq/faq177>, 8 pages.

* cited by examiner

PREDICTION AND TREATMENT OF IMMUNOTHERAPEUTIC TOXICITY

PRIORITY CLAIM

This application is a national phase application under 35 U.S.C. § 371 of International Application No. PCT/US2018/018594, filed Feb. 19, 2018, which claims benefit of priority to U.S. Provisional Application Ser. No. 62/461,455, filed Feb. 21, 2017, the entire contents of each of which are hereby incorporated by reference.

BACKGROUND

1. Field of the Disclosure

The present disclosure relates generally to the fields of medicine, oncology, and immunology. More particular, the disclosure relates to identification of markers for immunotherapy-related toxicity in the context of cancer treatments.

2. Background

Medical providers may soon be facing the possibility of curing patients of cancer at the expense of short-term or life-long autoimmune toxicity such as Crohn's disease, rheumatoid arthritis, or lupus as a result of their cancer therapy. Decades of oncology research have focused on utilizing the immune system to attack tumor cells. In the last several years, there have been remarkable advancements: drugs known as immunotoxins, chimeric antigen receptors and immune checkpoint inhibitors have proven effective for treating some cancers including melanoma and lung cancers Immune checkpoint inhibitors work by preventing cancer cells from turning T-cells (white blood cells that detect infections and abnormalities) off. This allows the T-cells to attack a tumor and stop it from growing. Based on promising results from recent clinical trials, immune checkpoint inhibitors will likely become available for many other cancers, including gynecologic malignancies, lymphomas, head-and-neck cancer, gastrointestinal tumors, and kidney cancer (Hamanishi et al., 2015; Ansell et al., 2015; McDermott et al., 2015; Early Breast Cancer Trials, 1998; Le et al., 2015) Immunotherapy is so effective that it could benefit millions of cancer patients worldwide every year.

However, a key element of this form of treatment remains poorly understood: toxicity (side effects). Oncologists understand and can anticipate the toxicity from traditional chemotherapy: hair loss after two treatment cycles, nausea/vomiting five-to-seven days after chemotherapy, low blood counts 10-14 days after chemotherapy. Physicians also know who is most likely to experience these complications, such as elderly patients and individuals with decreased liver or kidney function. However, the promising field of immunotherapy represents a completely new set of challenges. Because immune checkpoint inhibitors prevent T-cells from being turned off, these drugs could cause the immune system to attack healthy cells in addition to cancer cells and leave patients with an autoimmune reaction. Almost every organ can be involved including the brain (encephalitis), thyroid (hyper- or hypothyroidism), liver (hepatitis), and skin (dermatitis) (Howell et al., 2015). Prediction, detection and treatment of these toxicities is a new endeavor for oncologists. At present, physicians currently have no tools to predict who will experience these reactions, when they will occur, or how long they will last. Oncologists are seeing higher rates of autoimmune side effects than ever before, with up to 40 percent of patients experiencing clinically-serious events (Postow et al., 2015; Khan et al., 2016).

SUMMARY

Thus, in accordance with the present disclosure, there is provided a method of predicting/diagnosing immunotherapeutic toxicity in a human subject comprising (a) providing an antibody-containing sample from said subject; (b) assessing autoantibody level in said sample; and (c) predicting/diagnosing immunotherapy toxicity in said subject when the level of autoantibody is greater than populational average, and predicting lack of immunotherapy toxicity in said subject when the level of autoantibody is below a populational average. The sample may be a whole blood, serum, plasma, or other body fluid. The immunotherapy toxicity may be cancer immunotherapy toxicity. The autoantibody level may be assessed using a plurality of antigen in Table 1, or all antigens in Table 1. The autoantibody level may be assessed using a plurality of antigens in Table 2, or all antigens in Table 2. The autoantibody level may be assessed using a plurality of antigens in Table 1 and Table 2, or all antigens in Table 1 and Table 2.

Assessing may comprise ELISA, RIA, Western blot, microarray, such as fluorescence-based antibody screening protein microarray, bead array, cartridges, lateral flow, or line-probe assays. The method may further comprise repeating steps (a)-(c) at a second time point, thereby permitting assessment of a change in immunotherapeutic toxicity risk. The method may further comprise performing a control reaction with known autoantibody standards. The method may further comprise treating said subject with a cancer immunotherapy when said autoantibody level is below a populational average. The immunotherapy may comprise administration of an immune checkpoint inhibitor, an anti-CTLA4 antibody, an anti-PD1 antibody, an anti-PD1 ligand, a chimeric antigen receptor, or an immunotoxin. The method may further comprise treating said subject with a non-immunotherapy cancer treatment when said autoantibody level is above a populational average. The method may further comprising treating said subject with a cancer immunotherapy and a toxicity mitigating therapy, such as corticosteroids (e.g., prednisone, methylprednisolone, dexamethasone, budesonide), TNF inhibitors (e.g., infliximab), or hormone replacement (e.g., hydrocortisone, levothyroxine) when said autoantibody level is above a populational average. The immunotherapy may comprise administration of an immune checkpoint inhibitor, an anti-CTLA4 antibody, an anti-PD1 antibody, an anti-PD1 ligand, a chimeric antigen receptor, or an immunotoxin.

The method subject may have previously been diagnosed with an autoimmune disease. The subject may not have previously been diagnosed with an autoimmune disease. The subject may have lung cancer, melanoma, head & neck cancer, kidney cancer, or lymphoma, or bladder cancer. The method may further comprise assessing a rate of increase or decrease in autoantibody level. The method may further comprise stratifying said subject as having a relatively greater or lesser immunotherapy toxicity based on the number of different autoantibody specificities, with a great number of specificities correlating based on assessing a rate of increase or decrease in autoantibody level, and the method may further comprise selecting a mitigating/adjunct therapy based on the greater or lesser immunotherapy toxicity, such as where the adjunct therapy is a corticosteroid (e.g., prednisone, methylprednisolone, dexamethasone, budesonide), TNF inhibitor (e.g., infliximab), or hormone replacement therapy (e.g., hydrocortisone, levothyroxine). The method may also further comprise classifying immunotherapy toxicity based on organ or organ system in said subject, such as where the organ or organ system is skin (e.g., dermatitis), gastrointestinal tract (e.g., colitis), lung (e.g., pneumonitis), central/peripheral nervous system (e.g., encephalitis, myasthenia gravis), pituitary gland (e.g., hypophysitis), eye (endophthalmitis), heart (carditis), thyroid (thyroiditis/hyperthyroidism/hypothyroidism), adrenal gland (adrenalitis/adrenal insufficiency), liver (hepatitis), pancreas (pancreatitis, autoimmune type 1 diabetes), or kidney (nephritis). The subject may be further characterized as receiving a molecular targeted therapy, a chemotherapy, a chemoembolization, a radiotherapy, a radiofrequency ablation, a hormone therapy, a bland embolization, a surgery, or a second distinct immunotherapy.

In another embodiment, there is provided a method of treating a human subject with cancer comprising (a) providing an antibody-containing sample from said subject; (b) assessing autoantibody level in said sample; and (c) treating said subject with (i) a cancer immunotherapy when said autoantibody level is below populational average; (ii) a non-immunotherapy cancer treatment when said autoantibody level is above populational average; or (iii) a cancer immunotherapy and a toxicity mitigating therapy when said autoantibody level is above populational average. The sample may be a whole blood, serum, plasma, or other body fluid. The immunotherapy toxicity may be cancer immunotherapy toxicity. The autoantibody level may be assessed using a plurality of antigen in Table 1, or all antigens in Table 1. The autoantibody level may be assessed using a plurality of antigens in Table 2, or all antigens in Table 2. The autoantibody level may be assessed using a plurality of antigens in Table 1 and Table 2, or all antigens in Table 1 and Table 2.

Assessing may comprise ELISA, RIA, Western blot, microarray, such as fluorescence-based antibody screening protein microarray, bead array, cartridges, lateral flow, or line-probe assays. The method may further comprise repeating steps (a)-(c) at a second time point, thereby permitting assessment of therapeutic toxicity. The method may further comprise performing a control reaction with known autoantibody standards. The immunotherapy may comprise administration of an immune checkpoint inhibitor, an anti-CTLA4 antibody, an anti-PD1 antibody, an anti-PD1 ligand, a chimeric antigen receptor, or an immunotoxin. The immunotherapy may comprise a combination of multiple immunotherapeutic agents, or a combination of an immunotherapeutic agent and a non-immunotherapeutic agent.

The method subject may have previously been diagnosed with an autoimmune disease. The subject may not have previously been diagnosed with an autoimmune disease. The subject may have lung cancer, melanoma, head & neck cancer, kidney cancer, or lymphoma, or bladder cancer. The method may further comprise assessing a rate of increase or decrease in autoantibody level. The method may further comprise stratifying said subject as having a relatively greater or lesser immunotherapy toxicity based on the number of different autoantibody specificities, with a great number of specificities correlating based on assessing a rate of increase or decrease in autoantibody level, and the method may further comprise selecting a mitigating/adjunct therapy based on the greater or lesser immunotherapy toxicity, such as where the adjunct therapy is a corticosteroid (e.g., prednisone, methylprednisolone, dexamethasone, budesonide), TNF inhibitor (e.g., infliximab), or hormone replacement therapy (e.g., hydrocortisone, levothyroxine). The method may also further comprise classifying immunotherapy toxicity based on organ or organ system in said subject, such as where the organ or organ system is skin (e.g., dermatitis), lung (e.g., pneumonitis), central/peripheral nervous system (e.g., encephalitis, myasthenia gravis), pituitary gland (e.g., hypophysitis), eye (endophthalmitis), heart (carditis), gastrointestinal tract (colitis), thyroid (thyroiditis/hyperthyroidism/hypothyroidism), adrenal gland (adrenalitis/adrenal insufficiency), liver (hepatitis), pancreas (pancreatitis, autoimmune type 1 diabetes), or kidney (nephritis). The subject may be further characterized as receiving a molecular targeted therapy, a chemotherapy, a chemoembolization, a radiotherapy, a radiofrequency ablation, a hormone therapy, a bland embolization, a surgery, or a second distinct immunotherapy.

In yet a further embodiment, there is provided a method of determining whether a subject has recovered from immunotherapy toxicity comprising (a) providing a first antibody-containing sample from said subject following immunotherapy and the development of immunotherapy toxicity; (b) assessing autoantibody level in said first antibody-containing sample; (c) providing a second antibody-containing sample from said subject after immunotherapy toxicity has subsided; (d) assessing autoantibody level in said second antibody-containing sample; and (e) classifying said subject as suitable for further immunotherapy when autoantibody levels have dropped by at least 50% in said second antibody-containing sample as compared to said first antibody-containing sample. The method may further comprising treating said subject with an immunotherapy following step (e) when autoantibody levels have dropped by at least 50% in said second antibody-containing sample as compared to said first antibody-containing sample:

The sample may be a whole blood, serum, plasma, or other body fluid. The immunotherapy toxicity may be cancer immunotherapy toxicity. The autoantibody level may be assessed using a plurality of antigen in Table 1, using all antigens in Table 1, using a plurality of antigens in Table 2, using all antigens in Table 2, using a plurality of antigens in Table 1 and Table 2, or using all of antigens in Table 1 and Table 2. Assessing may comprise ELISA, RIA, Western blot, microarray, such as fluorescence-based antibody screening protein microarray, bead array, cartridges, lateral flow, or line-probe assays. The method may further comprise performing a control reaction with known autoantibody standards.

The immunotherapy may comprise administration of an immune checkpoint inhibitor, a chimeric antigen receptor, or an immunotoxin, may comprise administration of an anti-CTLA4 antibody, an anti-PD1 antibody, or an anti-PD1 ligand, may comprise a combination of multiple immunotherapeutic agents, or may comprise a combination of an immunotherapeutic agent and a non-immunotherapeutic agent. The subject may have previously been diagnosed with an autoimmune disease, or may not previously have been diagnosed with an autoimmune disease. The subject may have lung cancer, melanoma, head & neck cancer, kidney cancer, or lymphoma, or bladder cancer.

The method may further comprise assessing a rate of decrease in autoantibody level. The method may further comprise stratifying said subject as having a relatively greater or lesser risk of recurrent immunotherapy toxicity based on the number of different autoantibody specificities, with a great number of specificities correlating based on assessing a rate of increase or decrease in autoantibody level, and optionally further comprise selecting a mitigating/ adjunct therapy based on the greater or lesser immunotherapy toxicity, such as a corticosteroid (e.g., prednisone, methylprednisolone, dexamethasone, budesonide), TNF inhibitor (e.g., infliximab), or hormone replacement therapy (e.g., hydrocortisone, levothyroxine). The subject may be further characterized as receiving a molecular targeted therapy, a chemotherapy, a chemoembolization, a radiotherapy, a radiofrequency ablation, a hormone therapy, a bland embolization, a surgery, or a second distinct immunotherapy.

In still yet another embodiment, there is provided a method comprising (a) providing an antibody-containing sample from said subject having cancer and being treated with a cancer immunotherapy; (b) assessing autoantibody level in said sample; and (c) comparing the level of autoantibody to an age-, sex- and/or race-based populational average.

The sample may be whole blood, serum, plasma, or other body fluid. The method may assess autoantibody level using a plurality of antigen in Table 1, using all antigens in Table 1, using a plurality of antigens in Table 2, using all antigens in Table 2, using a plurality of antigens in Table 1 and Table 2, or all of antigens in Table 1 and Table 2. Assessing may comprise ELISA, RIA, Western blot, microarray, such as fluorescence-based antibody screening protein microarray, bead array, cartridges, lateral flow, or line-probe assays.

The method may further comprising repeating steps (a)-(c) at a second time point, thereby permitting assessment of a change in autoantibody levels over time. The method may further comprise performing a control reaction with known autoantibody standards.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

Cardolipin
Histone H1
Collagen III
FactorD
Collagen VI
Collagen II
Decorin-bovine
Genomic DNA
ssRNA
Histone H4
alpha-actinin
Collagen I
complement C3a
Cytochrome C
Histone-total
Chondroitin Sulfate
Chromatin
Collagen V
gP210
AGTR1
Heparan HSPG
Proteoglycan
dsDNA
ssDNA
Laminin
Collagen IV
Hemocyanin
CENP-B
A100
Alpha Fodrin (SPTAN1)
Prothrombin protein
PL-7
Scl-70
Thyroglobulin
b2-glycoprotein I
La/SSB
BPI
Jo-1
Elastin
Histone H2B
Topoisomerase I
Aggrecan
AQP4
Glycated Albumin
Sm/RNP
GP2
EBNA1
complement C7
complement C8
KU (P70/P80)
M2
complement C1q
Ro-52/SSA
complement C3
complement C5
complement C9

Figure 3:
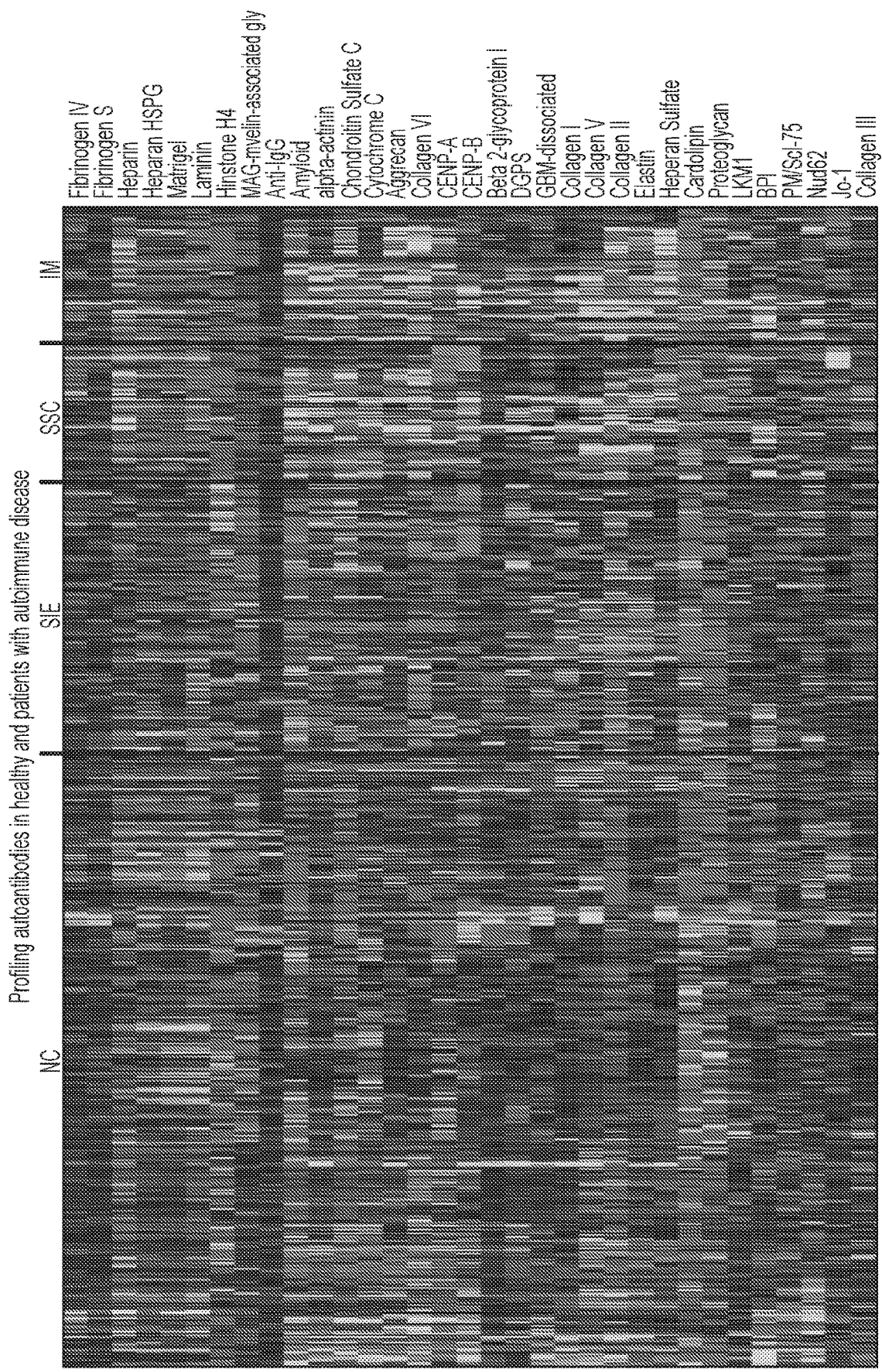
Figure 3:
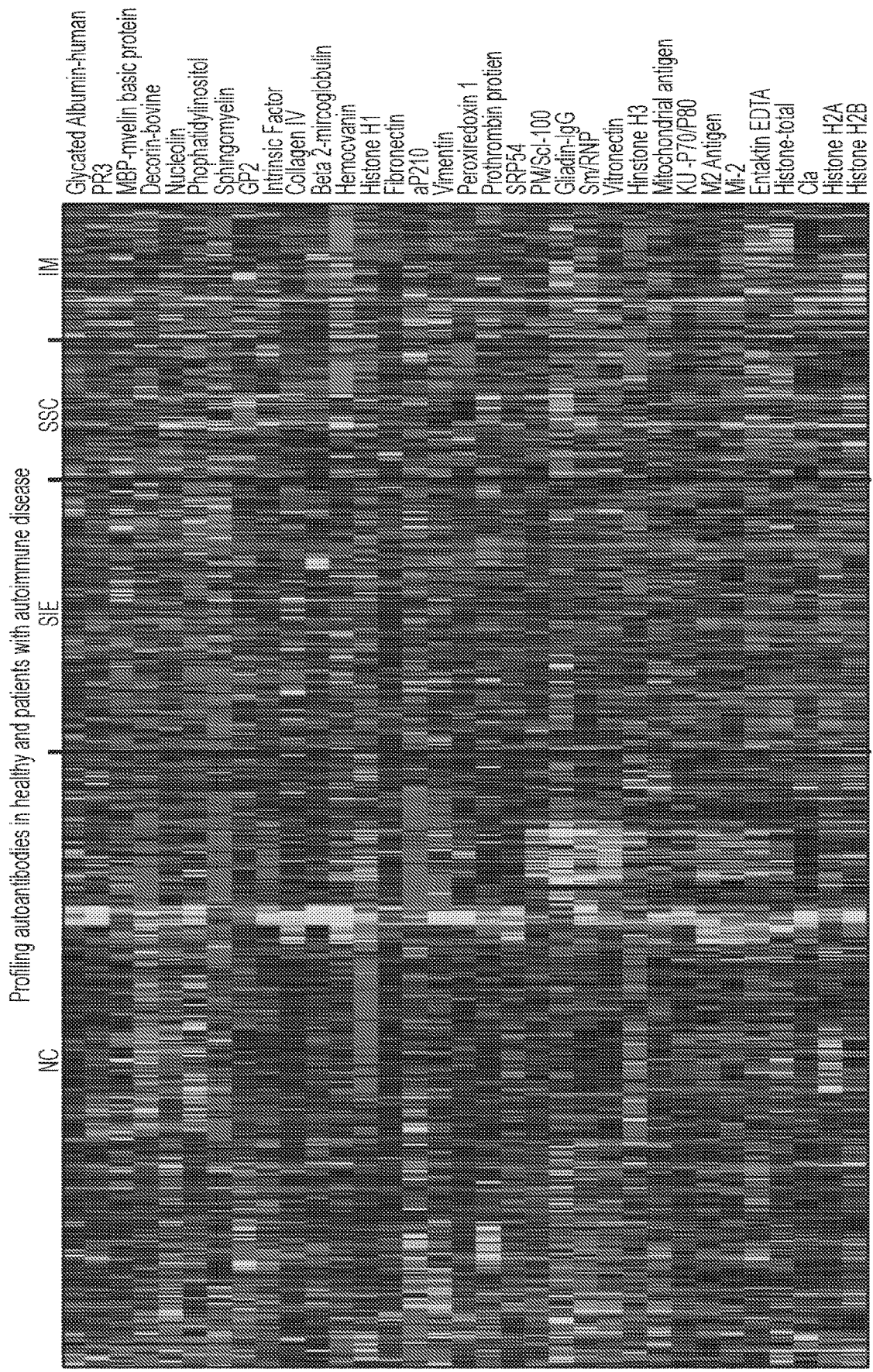
Figure 3:
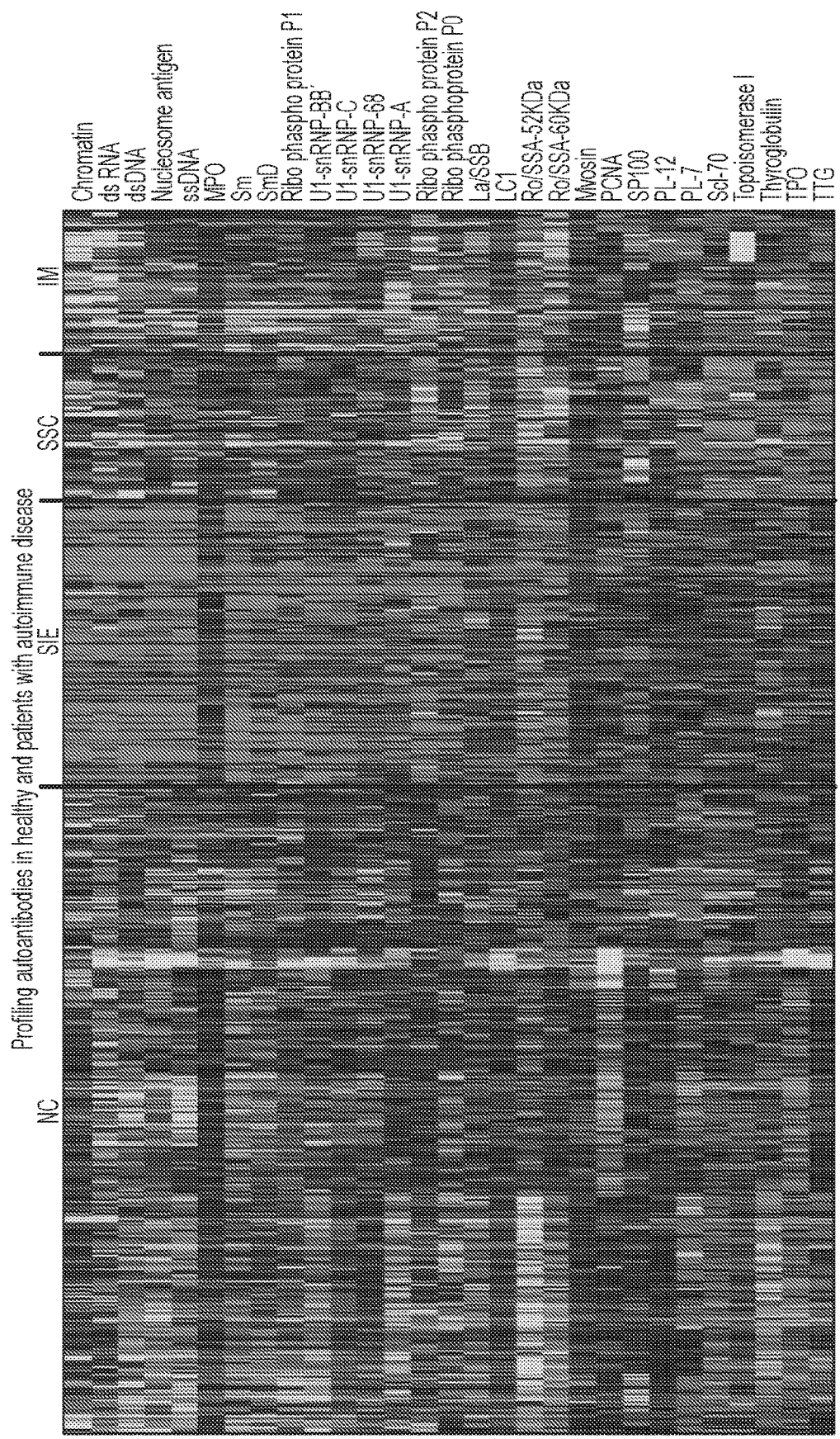

TTG
Mitochondrial antige
LC1
Fibrinogen IV
Ribo phasphoprotein P0
Fibrinogen S
TNFa
Peroxiredoxin 1
PM/Scl-75
Matrigel
Myelin-associated
glycoprotein
Myosin
PCNA
Muscarinic receptor
Vitronectin
Factor I
complement C3b
complement C4
complement C6
T1F1 GAMMA
FactorH
Ribo phasphoprotein P1
Intrinsic Factor
MDA5
MPO
SmD1
CRP antigen
FactorB
TPO
SP100
Vimentin
PL-12
Mi-2
Gliadin (IgG)
b2-microglobulin
PM/Scl-100
U1-snRNP-A
Nucleosome antigen
U1-snRNP-C
Nup62
GBM (disso)
Ribo phasphoprotein P2
Sm
U1-snRNP-68
Histone H2A
Heperan Sulfate
POLB
PR3
Factor P
Ro-60/SSA
Amyloid
SRP54
Phophatidylinositol
LKM1
SmD
SmD3
CENP-A
Entaktin EDTA
DGPS
Fibronectin
SmD2
U1-snRNP-BB'
Histone H3
Myelin basic protein
Sphingomyelin FIG. 3. Analysis of autoantigen reactivity in more than 600 sera with an array of more than 100 autoantigens. The list of antigens on the right side from top to bottom of the panel is as follows:
Histone H1
Amyloid
alpha-actinin
Chondroitin Sulfate
C
Aggrecan
Collagen VI
Cytochrome C
CENP-A
CENP-B
Decorin-bovine
Nucleolin
Collagen IV
Beta 2-glycoprotein
I
DGPS
GBM-dissociated
Collagen I
Collagen II
Collagen V
Elastin
Heperan Sulfate
Cardolipin
Proteoglycan
LKM1
Collagen III
Glycated Albumin
PR3
MBP
Phophatidylinositol
Sphingomyelin
Jo-1
Fibrinogen IV
Fibrinogen S
Heparin
Heperan HSPG
Matrigel
Laminin
Mitochondrial
antigen
BPI
GP2
Intrinsic Factor
Gliadin-IgG
Sm/RNP
Vitronectin
Entaktin EDTA
Histone-total
Hinstone H4
Hinstone H3
PL-12
PL-7
Beta 2-microglobulin
Hemocyanin
Peroxiredoxin 1
Prothrombin protein
SRP54
Myosin
PCNA
KU-P70/P80
M2 Antigen
Mi-2
C1q Histone H2B
Chromatin
ds RNA
dsDNA
Nucleosome
ssDNA
Histone H2A
MPO
Sm
SmD
Ribo phaspho protein P1
U1-snRNP-BB'
U1-snRNP-C
U1-snRNP-68
U1-snRNP-A
Ribo phaspho protein P2
Ribo phasphoprotein P0
La/SSB
LC1
Ro/SSA-52 KDa
Ro/SSA-60 KDa
SP100
PM/Scl-100
Scl-70
Topoisomerase I
Thyroglobulin
TPO
TTG
Fibronectin
Nup62
gP210
Vimentin
PM/Scl-75
MAG FIG. 4. Fifty auto-antibodies across healthy controls, patients without AE and patients with AE at baseline level.

Figure 5:
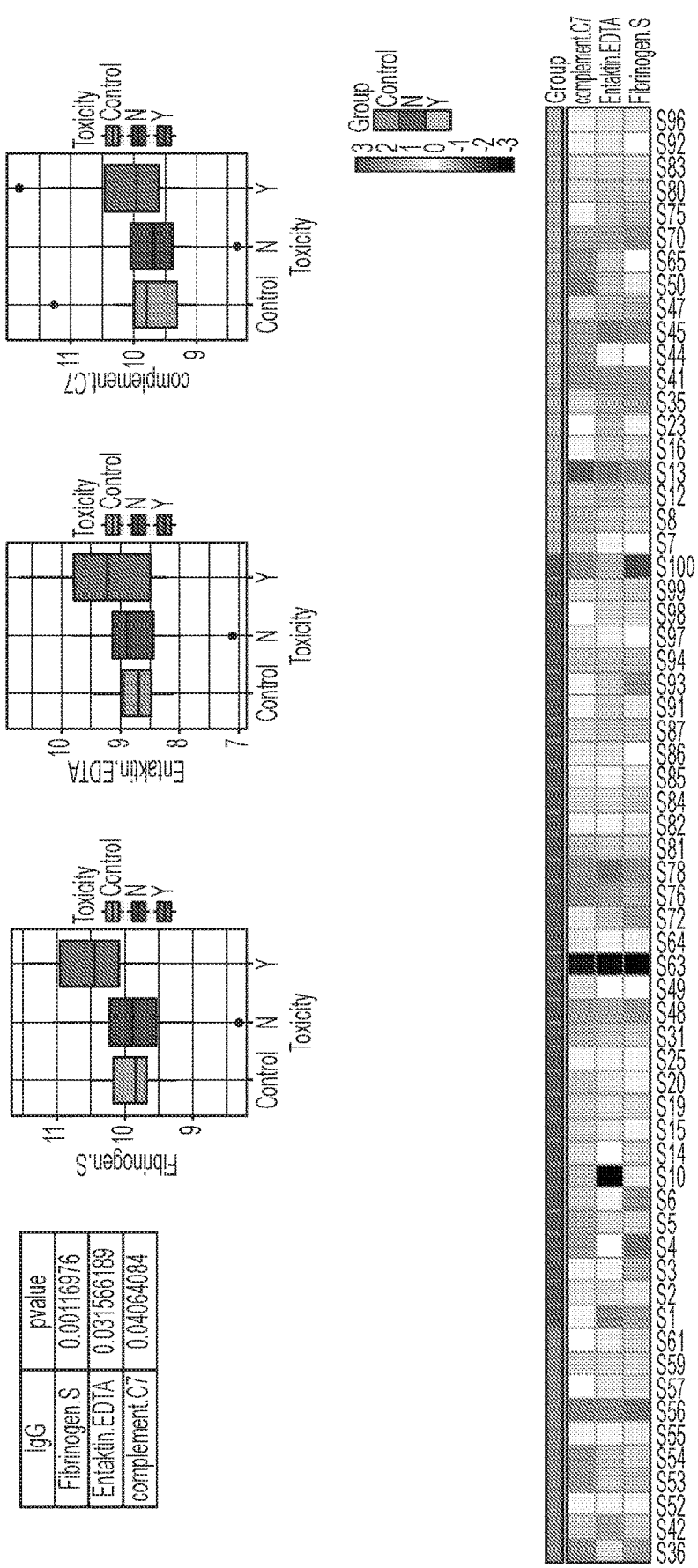

FIG. 5. Patients with AE have shown significantly elevated levels of auto-antibodies at baseline level as compared with patients without AE or healthy controls.

Figure 6:
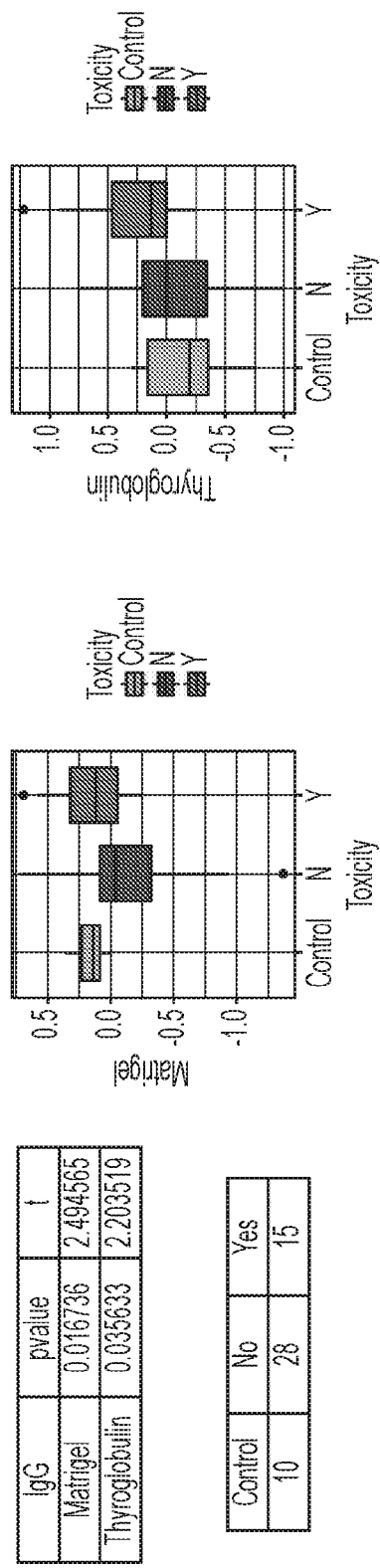

FIG. 6. Two out of 50 IgG are altered significantly two weeks post-treatment in the toxicity group versus the non-toxicity group. Graphs show log transformed-fold change in each group of patients two weeks versus baseline.

Figure 7:
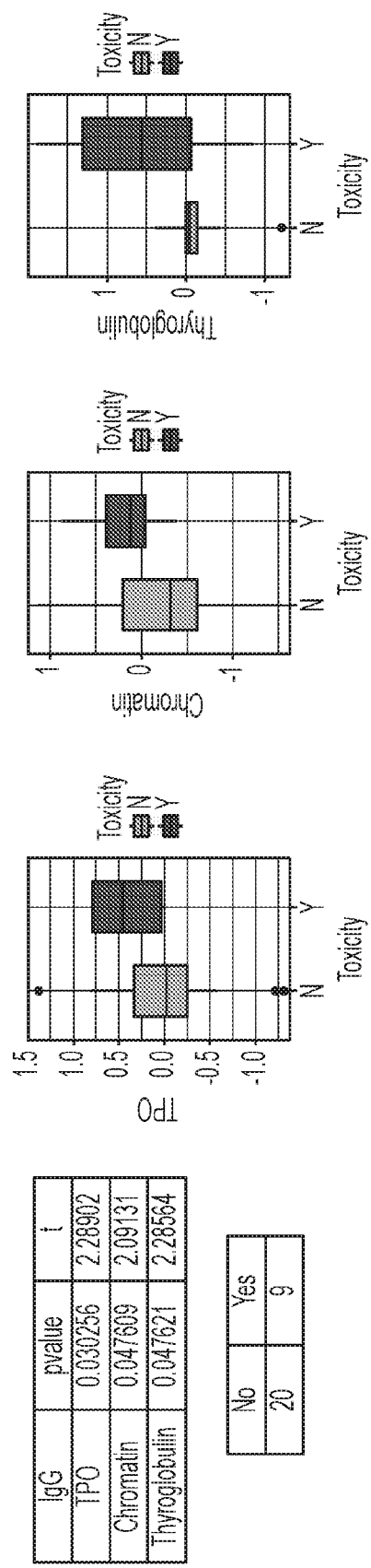

FIG. 7. Three out of 50 IgG are altered significantly six weeks post-treatment in the toxicity group versus non-toxicity group. Graphs show log transformed-fold change in each group of patients six weeks versus baseline.

Figure 8:
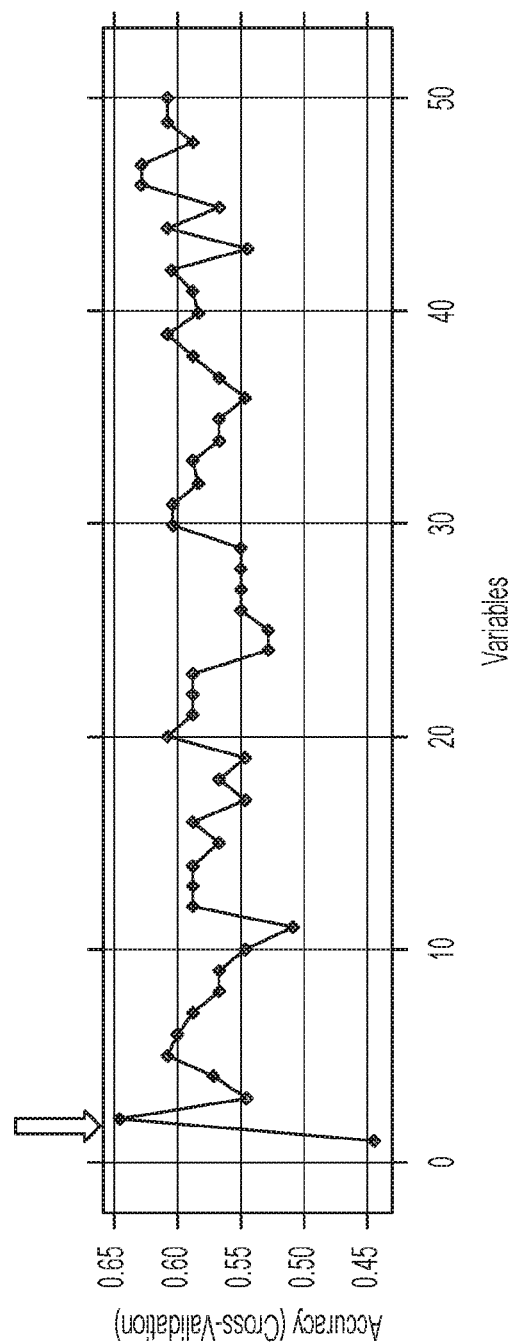
Figure 9:
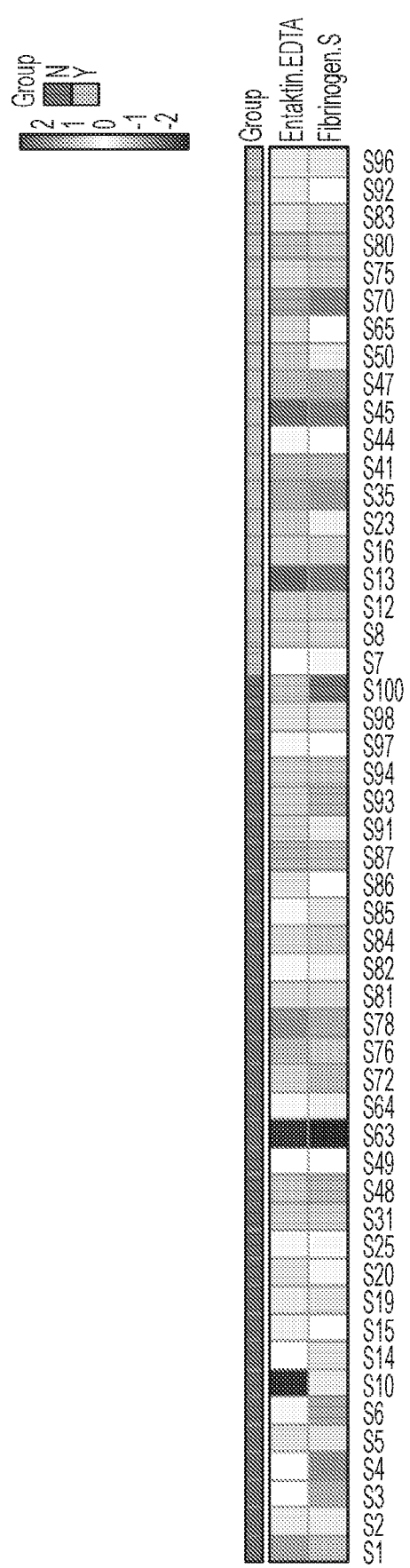

FIGS. 8-9. Random Forest Model in Caret Package to Select Important IgG That Could Predict Toxicity at Baseline Level. Based on a set of 32 patients without toxicity and 19 patients who developed toxicity.

DESCRIPTION OF ILLUSTRATIVE EMBODIMENTS

The currently used biomarkers for immunotherapy, which include PD-L1 expression, mutational burden and CD8 T-cell repertoire, are focused entirely on prediction of efficacy. There are no validated biomarkers that exist to predict toxicity, nor are there biomarkers to monitor the severity, chronology and response to anti-toxicity therapy in the immunotherapy setting.

Here, the inventors describe a blood test that examines antibodies to known autoantigens that is able to not only predict toxicity, but to monitor toxicity and guide immunotherapeutic selections. Furthermore, the same test can be used to monitor and guide treatment of immunotherapy toxicity.

These and other aspects of the disclosure are described in detail below.

I. IMMUNOTHERAPY AND RELATED TOXICITY

The emergence of cancer immunotherapy has introduced an entirely new set of unpredictable, potentially severe, and possibly permanent toxicities Immune checkpoint inhibitors targeting the cytotoxic T lymphocyte antigen 4 (CTLA4) and programmed death 1 (PD1) axes are transforming cancer treatment, with impressive clinical activity already leading to FDA approvals for melanoma, non-small cell lung cancer, renal cell carcinoma, Hodgkin's lymphoma, and bladder cancer. However, cancer immunotherapies also pose a risk for immune-related adverse events (irAEs). These diverse toxicities are problematic because they are entirely distinct from the toxicities oncologists have come to expect with conventional chemotherapy and molecularly targeted therapies.

Immune-mediated toxicities may impact almost every organ system, including brain, pituitary, thyroid, ocular, pulmonary, hepatic, intestinal, dermatologic, and adrenal (Topalian et al., 2012). In contrast to the well-characterized temporal patterns of classic chemotherapy toxicities such as alopecia, nausea/vomiting, and myelosuppression, the onset and duration of irAEs remains unpredictable. Recent studies indicate that up to 80% of individuals receiving checkpoint therapies experience some form of irAE, with about 35% of all patients requiring systemic corticosteroid treatments to mitigate these events, and up to 20% terminating their therapy due to irAEs (Horvat et al., 2015). These adverse responses convey substantial morbidity, incur considerable costs, and in some cases may preclude further use of these drugs. As immunotherapy use expands from major centers where pivotal trials have been conducted to smaller, isolated, and less experienced community sites, the ability to recognize and treat irAEs promptly may be challenged. With the FDA approval of combination PD1 and CLTA4 inhibition for melanoma in October 2015, and similar combinations currently under study in other diseases, rates and severity of irAEs may be even greater in the future. To date, no clinical, laboratory, or radiographic biomarkers can predict these toxicities.

The CTLA4 and PD1-PDL1 axes normally function to activate regulatory pathways that maintain peripheral tolerance to self-antigens (Allison et al., 1998a). The therapeutic benefit of inhibiting these regulatory systems is thought to result from the amplification of suppressed anti-tumor immune responses that are blocked by tumor-specific manipulations of the immune system (Gubin et al., 2014). However, these regulatory pathways are also intimately involved in the regulation of autoimmune and auto-aggressive immune responses (Allison et al., 1998b). As a result, it is quite likely that any extant autoimmune responses that are being regulated by these peripheral pathways might also become activated during checkpoint blockade therapy.

Figure 1:
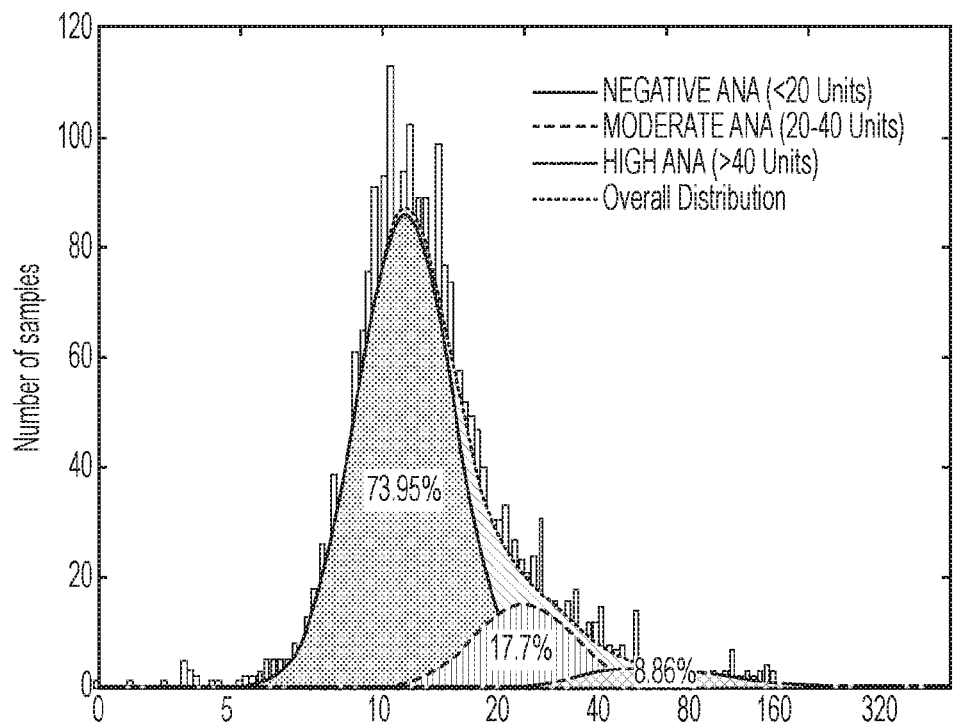
FIG. 1. (Top) Frequency distribution of ANA titers among 2,223 healthy donors. Three sub-distributions are present: ANA negative (74%), ANA moderate (18%), and ANA high (9%). (Bottom) Heat map illustrating the diverse array of autoantigens recognized by IgG antibodies from the sera of health individuals with benign autoimmunity. Antibody reactivity of 88 ANA negative (ELISA<20) (left) and 88 ANA positive (ELISA≥20) (right) for 34 auto-antigens. Strong reactivity is increasing red, while weaker is increasing green, relative to mean value (black) for all samples in the analysis. Scale is on the right.
Figure 1:
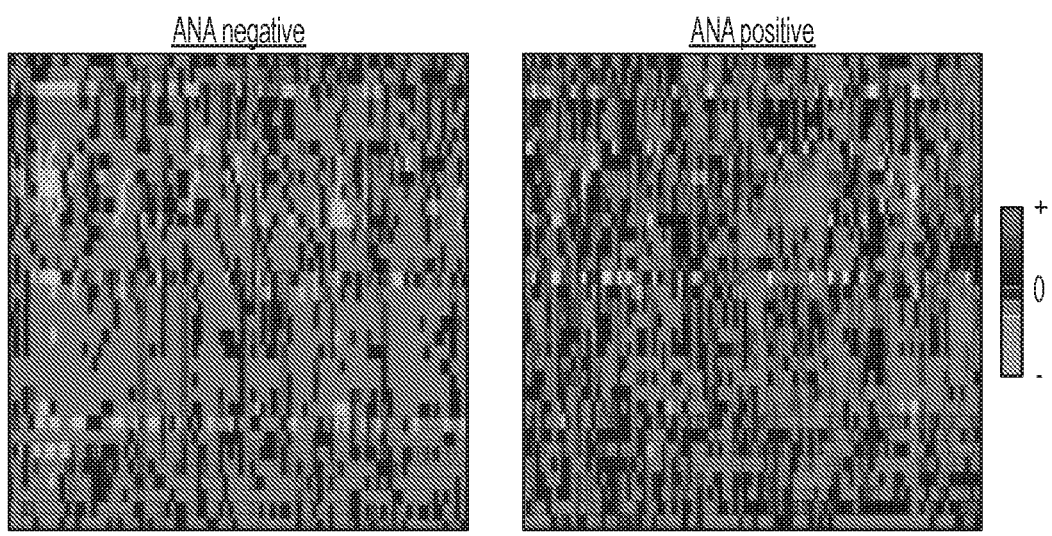

Autoimmune disease, in which the recognition of self-antigens by the immune system leads to severe damage to specific self-tissues, is estimated to affect almost 10% of the U.S. population (Cooper et al., 2009). A recent SEER-Medicare analysis suggests that the prevalence of these conditions may be even higher among individuals with cancer (Khan et al., 2016). Moreover, recent studies by the inventors and others have found that more than 26% of healthy individuals have strong IgG humoral immune responses to a variety of self-antigens, indicating that "benign" autoimmunity is much more common than autoimmune disease (FIG. 1) (Wandstradt et al., 2006; Li et al., 2011; Li and Wakeland, 2015; Tan et al., 1997). These findings indicate that many healthy individuals exhibit significant autoimmunity that is regulated in the peripheral immune system by pathways such as those triggered by CTLA-4 and PD1. Consistent with this observation, CTLA-4 and PD1 are both known to potentiate autoimmune disease, suggesting that the inhibition of these regulatory pathways aggravates pre-existing autoimmunity (Kristiansen et al., 2000; Romo-Tena et al., 2013; Gianchecchi et al., 2013). Based on this observation, the inventors hypothesize that checkpoint therapy irAEs often result from the activation of pre-existing autoimmunity.

II. AUTOIMMUNITY AND AUTOANTIGENS

A. Autoimmunity

Autoimmunity is defined as the system of immune responses of an organism against its own healthy cells and tissues. Any disease that results from such an aberrant immune response is termed an autoimmune disease. Prominent examples include celiac disease, diabetes mellitus type 1, sarcoidosis, systemic lupus erythematosus (SLE), Sjögren's syndrome, eosinophilic granulomatosis with polyangiitis, Hashimoto's thyroiditis, Graves' disease, idiopathic thrombocytopenic purpura, Addison's disease, rheumatoid arthritis (RA), psoriatic arthritis, ankylosing spondylitis, polymyositis (PM), and dermatomyositis (DM). Autoimmune diseases are very often treated with steroids.

The misconception that an individual's immune system is totally incapable of recognizing self-antigens is not new. Paul Ehrlich, at the beginning of the twentieth century, proposed the concept of horror autotoxicus, wherein a "normal" body does not mount an immune response against its own tissues. Thus, any autoimmune response was perceived to be abnormal and postulated to be connected with human disease. Now, it is accepted that autoimmune responses are an integral part of vertebrate immune systems (sometimes termed "natural autoimmunity"), normally prevented from causing disease by the phenomenon of immunological tolerance to self-antigens.

While a high level of autoimmunity is unhealthy, a low level of autoimmunity may actually be beneficial. Taking the experience of a beneficial factor in autoimmunity further, one might hypothesize with intent to prove that autoimmunity is always a self-defense mechanism of the mammalian system to survive. The system does not randomly lose the ability to distinguish between self and non-self; the attack on cells may be the consequence of cycling metabolic processes necessary to keep the blood chemistry in homeostasis. Autoimmunity may have a role in allowing a rapid immune response in the early stages of an infection when the availability of foreign antigens limits the response (i.e., when there are few pathogens present).

Certain individuals are genetically susceptible to developing autoimmune diseases. This susceptibility is associated with multiple genes plus other risk factors. Genetically predisposed individuals do not always develop autoimmune diseases. Three main sets of genes are suspected in many autoimmune diseases. These genes are related to immunoglobulins, T-cell receptors and the major histocompatibility complex (MHC). The first two, which are involved in the recognition of antigens, are inherently variable and susceptible to recombination. These variations enable the immune system to respond to a very wide variety of invaders, but may also give rise to lymphocytes capable of self-reactivity. The contributions of genes outside the MHC complex remain the subject of research, in animal models of disease and in patients.

A person's sex also seems to have some role in the development of autoimmunity; that is, most autoimmune diseases are sex-related. Nearly 75% of the more than 23.5 million Americans who suffer from autoimmune disease are women, although it is less-frequently acknowledged that millions of men also suffer from these diseases. The inventors showed that publication that, among patients with lung cancer, those with autoimmune disease were more likely to be women (Khan et al., 2016). According to the American Autoimmune Related Diseases Association (AARDA), autoimmune diseases that develop in men tend to be more severe. A few autoimmune diseases that men are just as or more likely to develop as women include: ankylosing spondylitis, type 1 diabetes mellitus, granulomatosis with polyangiitis, Crohn's disease, Primary sclerosing cholangitis and psoriasis.

An interesting inverse relationship exists between infectious diseases and autoimmune diseases. In areas where multiple infectious diseases are endemic, autoimmune diseases are quite rarely seen. The reverse, to some extent, seems to hold true. The hygiene hypothesis attributes these correlations to the immune manipulating strategies of pathogens. Whilst such an observation has been variously termed as spurious and ineffective, according to some studies, parasite infection is associated with reduced activity of autoimmune disease. The putative mechanism is that the parasite attenuates the host immune response in order to protect itself. This may provide a serendipitous benefit to a host that also suffers from autoimmune disease. The details of parasite immune modulation are not yet known, but may include secretion of anti-inflammatory agents or interference with the host immune signaling.

A paradoxical observation has been the strong association of certain microbial organisms with autoimmune diseases. For example, *Klebsiella pneumoniae* and coxsackievirus B have been strongly correlated with ankylosing spondylitis and diabetes mellitus type 1, respectively. This has been explained by the tendency of the infecting organism to produce super-antigens that are capable of polyclonal activation of B-lymphocytes, and production of large amounts of antibodies of varying specificities, some of which may be self-reactive.

Certain chemical agents and drugs can also be associated with the genesis of autoimmune conditions, or conditions that simulate autoimmune diseases. The most striking of these is the drug-induced lupus erythematosus. Usually, withdrawal of the offending drug cures the symptoms in a patient. Cigarette smoking is now established as a major risk factor for both incidence and severity of rheumatoid arthritis. This may relate to abnormal citrullination of proteins, since the effects of smoking correlate with the presence of antibodies to citrullinated peptides.

B. Autoantigen Microarray Super Panel (128 Antigen Panel)

An autoantigen is defined as normal protein or protein complex (and sometimes DNA or RNA) that is recognized by the immune system of patients suffering from a specific autoimmune disease. These antigens should not be, under normal conditions, the target of the immune system, but their associated T cells are not deleted and instead attack.

Autoantigen array super panel I contains 128 autoantigens and various internal controls. The autoantigens in this panel include most of nuclear antigens, cytoplasmic antigens, membrane antigen, phospholipid antigens, as well as some novel autoantigens identified from serum and tissues. The antigens in the Super Panel are listed below:

TABLE 1

| Autoantigen SuperPanel |
| --- |
| A100 |
| Aggrecan |
| AGTR |
| Alpha Fodrin (SPTAN1) |
| alpha-actinin |
| Amyloid |
| AQP4 recombinant |
| BPI |
| Cardolipin |
| CENP-A |
| CENP-B |
| Chondroitin Sulfate C |
| Chromatin |
| Collagen I |
| Collagen II |
| Collagen III |
| Collagen IV |
| Collagen V |
| Collagen VI |
| complement C1q |
| complement C3 |
| complement C3a |
| complement C3b |
| complement C4 |
| complement C5 |
| complement C6 |
| complement C7 |
| complement C8 |
| complement C9 |
| CRP antigen |
| Cytochrome C |
| Decorin-bovine |
| DGPS |
| dsDNA |
| EBNA1 |
| Elastin |
| Entaktin EDTA |
| Factor I |
| Factor P |
| FactorB |
| FactorD |
| FactorH |
| Fibrinogen IV |
| Fibrinogen S |
| Fibronectin |
| GBM (disso) |
| Gliadin (IgG) |
| Glycated Albumin |
| GP2 |
| gP210 |
| H1 |
| H2A |
| H2B |
| H3 |
| H4 |
| Hemocyanin |
| Heparan HSPG |
| Heparin |
| Heperan Sulfate |
| Histone-total |
| human genomic DNA |
| Intrinsic Factor |
| Jo-1 |
| KU (P70/P80) |
| La/SSB |
| Laminin |
| LC1 |
| LKM1 |
| M2 Antigen |

TABLE 1-continued

| Autoantigen SuperPanel |
| --- |
| Matrigel |
| MDA5 |
| Mi-2 |
| Mitochondrial antigen |
| MPO |
| Muscarinic receptor |
| Myelin basic protein (MBP) |
| Myelin-associated glycoprotein-FC (MAG) |
| Myosin |
| Nucleolin |
| Nucleosome antigen |
| Nup62 |
| PCNA |
| Peroxiredoxin 1 |
| Phophatidylinositol |
| PL-12 |
| PL-7 |
| PM/Scl-100 |
| PM/Scl-75 |
| POLB |
| PR3 |
| Proteoglycan |
| Prothrombin protien |
| Ribo phaspho protein P1 |
| Ribo phaspho protein P2 |
| Ribo phasphoprotein P0 |
| Ro/SSA (52 KDa) |
| Ro/SSA (60 KDa) |
| Scl-70 |
| Sm |
| Sm/RNP |
| SmD |
| SmD1 |
| SmD2 |
| SmD3 |
| SP100 |
| Sphingomyelin |
| SRP54 |
| ssDNA |
| ssRNA |
| T1F1 GAMMA |
| Thyroglobulin |
| TNFa |
| Topoisomerase I |
| TPO |
| TTG |
| U1-snRNP-68 |
| U1-snRNP-A |
| U1-snRNP-BB' |
| U1-snRNP-C |
| Vimentin |
| Vitronectin |
| β2-glycoprotein I |
| β2-microglobulin |
| IgG Control |
| anti-Ig |

The autoantigens are printed on 16-pad FAST slide. Each chip contains 16 identical arrays and can process 15 samples and one PBS control.

TABLE 2

| Autoantigen Microarray Panel IV |
| --- |
| CMV-G |
| CMV-M |
| CMV EXT-2 |
| CMV GRADE III |
| HEPATITIS A |
| HAV CONCENTRATE |
| HSV-1 |
| HSV-2 |
| RUBEOLA |
| RSV |

TABLE 2-continued

Autoantigen Microarray Panel IV

ROTAVIRUS SA-11
RUBELLA VIRUS GRADE III
RUBELLA VIRUS GRADE IV
RUBELLA GRADE IV
RSVP
TOXOPLASMA Antigen
VZV
VZV GRADE II
HUMAN AZUROCDIN
House Dust
Dog Dander
Dog Epithelia
Beef_Bos taurus
Shrimp_Penacidae
Peanut_Arachis hypogaea
Wheat, Whole_Triticum aestivum
Mite, House Dust_Blomia tropicalis
Bermuda_Cynodon dactylon
Cedar, Red_Juniper rus virginiana
Plantain, English_Plantago lanceolata
Honey Bee_Apis mellifera
3-hydroxy-3-methylglutaryl-coenzyme A reductase
Aminoacyl-tRNA Synthetase
Asparaginyl-tRNA Synthetase(KS)
Glycyl-tRNA Synthetase(EJ)
Lysyl-tRNA Synthetase
Phenylalanyl-tRNA Synthetase 2
Human Cytosolic 5'-nucleotidase 1A
glutaminyl-tRNA Synthetase
MORC family CW-type zinc finger 3 (MORC3)
signal recognition particle 14 kDa
SUMO1 activating enzyme subunit 1(SAE1)
tryptophanyl-tRNA Synthetase(WARS)
tyrosyl-tRNA Synthetase(YARS)
ubiquitin-like modifier activating anzyme 2(UBA2)
NY-ESO-1
Prostatic Acid Phosphatase
Prostate Specific Membrane Antigen
MAGEA3
FOLH1
PSA
CA 125
CEA
PSMA/FOLH1/NAALADase 1
Myosin Light Chain
Muscarinic receptor
Albumin Bovine fraction V
AQP4
DNA Polymerase beta Protein
EBV EBNA1
AGTR1(angiotension receptor1)
Collagenase A
Collagenase D
Tetanus toxin
Ig Control
Anti-Ig The autoantigens are printed on 16-pad FAST slide. Each chip contains 1.6 identical arrays and can process 15 samples and one PBS control.

When used herein, the term "populational average" may refer to the population at large, i.e., meaning all patients in the local, regional or national population in which the subject resides. The term may also refer to all cancer patients in the local, regional or national population in which the subject resides, including particular cancer subtypes of the patient. The term may also refer to all healthy patients in the local, regional or national population in which the subject resides. Alternatively, rather than utilized a populational average, the measure of risk may be associated with 1 or 2 standard deviations of the populational average, or the top 1/3 of populations antibody measures.

III. IMMUNOTHERAPY AND TREATMENT OF IMMUNOTHERAPEUTIC TOXICITY

A. Immunotherapies

Immunotherapy is defined as the treatment of disease by inducing, enhancing, or suppressing an immune response Immunotherapies designed to elicit or amplify an immune response are classified as activation immunotherapies, while immunotherapies that reduce or suppress are classified as suppression immunotherapies Immunomodulatory regimens often have fewer side effects than existing drugs, including less potential for creating resistance when treating microbial disease.

Cancer immunotherapy is an example of an activation immunotherapy. Cell-based immunotherapies are effective for some cancers Immune effector cells such as lymphocytes, macrophages, dendritic cells, natural killer cells (NK Cell), cytotoxic T lymphocytes (CTL), etc., work together to defend the body against cancer by targeting abnormal antigens expressed on the surface of tumor cells. Therapies such as granulocyte colony-stimulating factor (G-CSF), interferons, imiquimod and cellular membrane fractions from bacteria are licensed for medical use. Others including IL-2, IL-7, IL-12, various chemokines, synthetic cytosine phosphate-guanosine (CpG) oligodeoxynucleotides and glucans are involved in clinical and preclinical studies.

Cancer immunotherapy attempts to stimulate the immune system to destroy tumors. A variety of strategies are in use or are undergoing research and testing. Randomized controlled studies in different cancers resulting in significant increase in survival and disease free period have been reported and its efficacy is enhanced by 20-30% when cell-based immunotherapy is combined with conventional treatment methods.

For example, extraction of G-CSF lymphocytes from the blood and expanding in vitro against a tumor antigen before reinjecting the cells with appropriate stimulatory cytokines can destroy the tumor cells that express the antigen. BCG immunotherapy for early stage (non-invasive) bladder cancer instills attenuated live bacteria into the bladder and is effective in preventing recurrence in up to two thirds of cases. Topical immunotherapy utilizes an immune enhancement cream (imiquimod) which produces interferon, causing the recipient's killer T cells to destroy warts, actinic keratoses, basal cell cancer, vaginal intraepithelial neoplasia, squamous cell cancer, cutaneous lymphoma, and superficial malignant melanoma. Injection immunotherapy ("intralesional" or "intratumoral") uses mumps, candida, the HPV vaccine or trichophytin antigen injections to treat warts (HPV-induced tumors). Adoptive cell transfer has been tested on lung and other cancers.

Dendritic cells can be stimulated to activate a cytotoxic response towards an antigen. Dendritic cells, a type of antigen presenting cell, are harvested from the person needing the immunotherapy. These cells are then either pulsed with an antigen or tumor lysate or transfected with a viral vector, causing them to display the antigen. Upon transfusion into the person, these activated cells present the antigen to the effector lymphocytes (CD4+ helper T cells, cytotoxic CD8+ T cells and B cells). This initiates a cytotoxic response against tumor cells expressing the antigen (against which the adaptive response has now been primed). The cancer vaccine Sipuleucel-T is one example of this approach.

Adoptive cell transfer in vitro cultivates autologous, extracted T cells for later transfusion. The T cells may already target tumor cells. Alternatively, they may be genetically engineered to do so. These T cells, referred to as tumor-infiltrating lymphocytes (TIL), are multiplied using high concentrations of Interleukin-2, anti-CD3 and alloreactive feeder cells. These T cells are then transferred back into the person along with administration of IL-2 to further boost their anti-cancer activity.

Before reinfusion, lymphodepletion of the recipient is required to eliminate regulatory T cells as well as unmodified, endogenous lymphocytes that compete with the transferred cells for homeostatic cytokines. Lymphodepletion can be achieved by total body irradiation. Transferred cells multiplied in vivo and persisted in peripheral blood in many people, sometimes representing levels of 75% of all $CD8^+$ T cells at 6-12 months after infusion. As of 2012, clinical trials for metastatic melanoma were ongoing at multiple sites.

Autologous immune enhancement therapy use a person's own peripheral blood-derived natural killer cells, cytotoxic T lymphocytes and other relevant immune cells are expanded in vitro and then reinfused. The therapy has been tested against Hepatitis C, Chronic fatigue syndrome and HHV6 infection.

Genetically engineered T cells are created by harvesting T cells and then infecting the T cells with a retrovirus that contains a copy of a T cell receptor (TCR) gene that is specialized to recognize tumor antigens. The virus integrates the receptor into the T cells' genome. The cells are expanded non-specifically and/or stimulated. The cells are then reinfused and produce an immune response against the tumor cells. The technique has been tested on refractory stage IV metastatic melanomas and advanced skin cancer.

B. Immunotherapeutic Toxicity and Treatment Considerations

In general, management of irAEs includes the early recognition and the use of immunosuppressive agents, such as steroids or anti-TNF-α, based on the severity of the irAEs. Most toxicities are mild to moderate, involve mainly skin and GI events, while treatment-related deaths are very rare. Furthermore, the incidence and severity of toxicities is, in some cases, dose related.

The onset and outcome of irAEs seems to vary according to the organs involved and, although most occur within the first 3 months of treatment, there are some specific toxicities reported months after the end of therapy. The majority of irAEs, however, are seen within the first 3 months of therapy, and the majority also resolve within this same time frame. It is evident that dermatologic irAEs appear usually after 2-3 weeks and typically resolve quickly, GI and hepatic irAEs appear after 6-7 weeks, while endocrinopathies can be diagnosed even after 9 weeks and may take some time to resolve, and rarely may be irreversible.

Skin toxicity, such as rash and pruritus, is common. After eliminating other causes, topical and/or oral steroid therapy can be used, with reduction or skipping of one or more immunotherapy dosings if the condition does not resolve. Only for severe events, will high-dose steroid therapy given intravenously, followed by oral steroids on improvement, be used.

GI adverse events such as diarrhea and colitis are at least as common as skin toxicity. Most treatment guidelines include grading and severity assessment, followed by antidiarrheic diet and hydration and monitor closely until resolution. Treatment with oral budesonide or other moderate dose steroid can be initiated if the condition persists. In serious/severe cases, treatment with high dose steroids is required. If no response is seen in one week, then immunosuppressive therapy with anti-TNF inhibitors (5 mg/kg remicade, infliximab) may be started.

Liver toxicity, while somewhat more rare, is not uncommon. If hepatotoxicity occurs, the patient should be admitted to the hospital for evaluation and close monitoring and immunotherapy stopped until hepatotoxicity is resolved. Intravenous corticosteroids should be started, and if no improvement, an immunosuppressive agent may be added, further supplemented by tacrolimus if needed.

Endocrine toxicity is fairly common advent in patients receiving immunotherapy. Therefore, routine monitoring of thyroid function at least during treatment and close monitoring of other endocrine function tests is now recommended. Abnormalities are usually easily corrected with hormone replacement. Hypophysitis can remain undetected since the symptoms might be vague, such as fatigue, hypotension or myalgias, and may be missed unless the examining clinician is aware of the risk. Management includes hormone replacement, according to hormone dysfunction (thyroxine, testosterone, estradiol, or more commonly steroids, such as hydrocortisone). Endocrinopathies in general can be managed with a short course of high dose steroid treatment, along with appropriate hormone replacement.

Autoimmune neuropathies are rare but do occur, ranging from mild paresthesias to severe neurologic syndromes. If neuropathy is considered to be significant, immunotherpay should be stopped and treatment with oral or i.v. steroids started. Ocural toxicity is also rare and it includes conjunctivitis or uveitis, which usually respond well to topical steroid treatment.

Other less common toxicities include pneumonitis (prompt high-dose steroid initiation and close monitoring of symptoms, oxygen needs and radiological findings), renal toxicity (close monitoring of creatinine, steroid administration and immunotherapy interruption until resolution), and myocarditis.

IV. IMMUNODETECTION METHODS

In still further embodiments, the present disclosure concerns immunodetection methods for binding, purifying, removing, quantifying and otherwise generally detecting autoantibodies.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of auto-antibodies directed to specific viral epitopes in samples also is provided. The steps of various useful immunodetection methods have been described in the scientific literature, such as, e.g., Doolittle and Ben-Zeev (1999), Gulbis and Galand 0993), De Jager et al. (1993), Nakamura et al. (1987) and Wild, D. (2013). In general, the immunobinding methods include obtaining a sample suspected of containing an autoantibody, and contacting the sample with a first antigen in accordance with the present disclosure, as the case may be, under conditions effective to allow the formation of immunocomplexes.

The immunobinding methods also include methods for detecting and quantifying the amount of autoantibodies in a sample and the detection and quantification of any immune complexes formed during the binding process. Here, one would obtain a sample suspected of containing autoantibodies, and contact the sample with an antigen that binds the autoantibodies or components thereof, followed by detecting and quantifying the amount of immune complexes formed under the specific conditions. In terms of antibody detection, the biological sample analyzed may be any sample that is suspected of containing autoantibodies, such as a tissue section or specimen, a homogenized tissue extract, a biological fluid, including blood and serum, or a secretion, such as feces or urine.

Contacting the chosen biological sample with the antigen under effective conditions and for a period of time sufficient to allow the formation of immune complexes (primary immune complexes) is generally a matter of simply adding the antigen composition to the sample and incubating the mixture for a period of time long enough for the antigen to form immune complexes with, i.e., to bind to autoantibodies present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple and direct sense, are binding assays. Certain preferred immunoassays are the various types of enzyme linked immunosorbent assays (ELISAs) and radioimmunoassays (RIA) known in the art Immunohistochemical detection using tissue sections is also particularly useful. However, it will be readily appreciated that detection is not limited to such techniques, and western blotting, dot blotting, FACS analyses, and the like may also be used.

In one exemplary ELISA, the antigens are immobilized onto a selected surface exhibiting protein affinity, such as a well in a polystyrene microtiter plate. Then, a test composition suspected of containing the autoantibodies is added to the wells. After binding and washing to remove non-specifically bound immune complexes, the bound autoantibodies may be detected. Detection may be achieved by the addition of an antibody that binds the Fc portion of the autoantibodies and that is linked to a detectable label. This type of ELISA is a simple "sandwich ELISA."

In another exemplary ELISA, the samples suspected of containing the autoantibodies are immobilized onto the well surface and then contacted with antigen. After binding and washing to remove non-specifically bound immune complexes, the bound antigens are detected. Again, the immune complexes may be detected using a second antibody that has binding affinity for the antigen at an alternative site, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with antigen, one will generally incubate the wells of the plate with a solution of the antigen, either overnight or for a specified period of hours. The wells of the plate will then be washed to remove incompletely adsorbed material. Any remaining available surfaces of the wells are then "coated" with a non-specific protein that is antigenically neutral with regard to the test antisera. These include bovine serum albumin (BSA), casein or solutions of milk powder. The coating allows for blocking of non-specific adsorption sites on the immobilizing surface and thus reduces the background caused by non-specific binding of autoantibodies onto the surface.

In ELISAs, it is probably more customary to use a secondary or tertiary detection means rather than a direct procedure. Thus, after binding of an antigen to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG)

or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

In another embodiment, the present disclosure contemplates the use of competitive formats. This is particularly useful in the detection of autoantibodies in sample. In competition based assays, an unknown amount of analyte or competing antibody is determined by its ability to displace a known amount of labeled antibody or analyte. Thus, the quantifiable loss of a signal is an indication of the amount of unknown antibody or analyte in a sample.

Here, the inventors propose the use of labeled autoantibodies to determine the amount of autoantibodies in a sample. The basic format would include contacting a known amount of autoantibodies (linked to a detectable label) with the antigen. The antigen is preferably attached to a support. After binding of the labeled monoclonal antibody to the support, the sample is added and incubated under conditions permitting any unlabeled autoantibodies in the sample to compete with, and hence displace, the labeled monoclonal antibody. By measuring either the lost label or the label remaining (and subtracting that from the original amount of bound label), one can determine how much non-labeled antibody is bound to the support, and thus how much autoantibody was present in the sample.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF, but are far more fragile and do not stand up well to repeated probing. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Immunodetection Kits

In still further embodiments, the present disclosure concerns immunodetection kits for use with the immunodetection methods described above. The immunodetection kits will thus comprise, in suitable container means, one or more antibodies that bind to autoantigens, and optionally an immunodetection reagent.

In certain embodiments, the antibody may be pre-bound to a solid support, such as a column matrix and/or well of a microtiter plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of the antigen or antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

In addition, there are multiple commercialized multiplex assays that are used in clinical laboratories to evaluate for autoantigens and/or allergens. These formats include spotted microarrays, bead/particle based assays (e.g., Luminex), line probe (e.g., Innogenetics), and cartridges (Hitachi Optigen).

V. EXAMPLES

The following examples are included to demonstrate preferred embodiments. It should be appreciated by those of skill in the art that the techniques disclosed in the examples that follow represent techniques discovered by the inventors to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Figure 2:
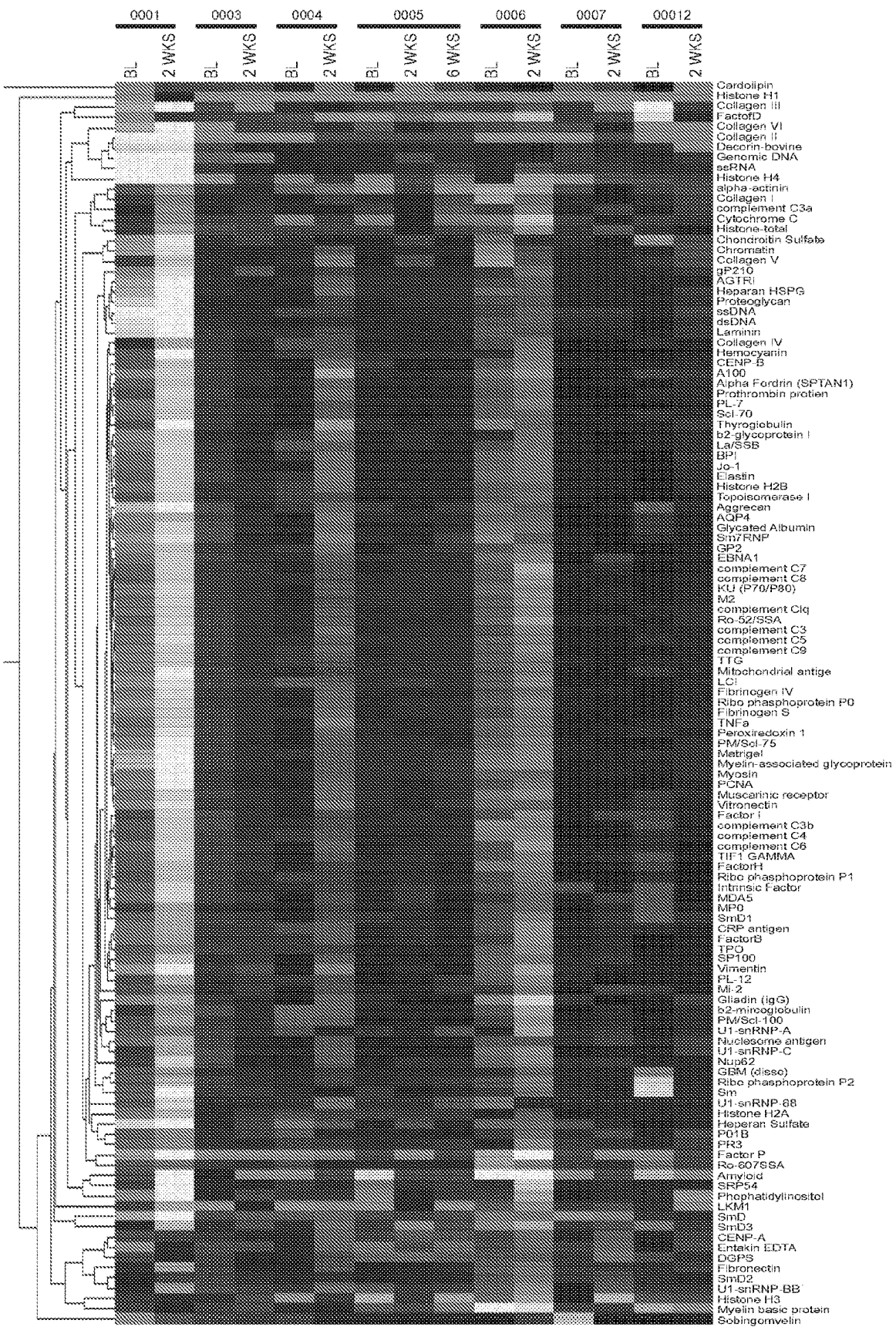
FIG. 2. Paired IgG autoantibody profiles from patients before and after immune checkpoint inhibitor therapy. Scale: low, blue; moderate, black; high, yellow. Note that patients with highest baseline autoimmunity (patients 1, 4, 6) also appear to have the greatest proportional increase in autoantibodies after treatment exposure. The list of antigens on the right side from top to bottom of the panel is as follows.

In addition to profiling autoantibody profiles in healthy individuals (FIG. 1), the inventors have performed similar analyses in patients with cancer undergoing immune checkpoint inhibitor therapy (FIG. 2). With pilot funding from the David M. Crowley Foundation and the Carlson Trust, the inventors collected sera on patients receiving immune checkpoint inhibitor therapy for cancer diagnoses. These data demonstrate that, as hypothesized, there is considerable variation in baseline autoimmunity among patients (none of whom had a pre-existing clinical autoimmune diagnosis) and that these profiles may change in response to exposure to immunotherapy. Consistent with our hypothesis, dynamic increases in autoantibody profiles are particularly apparent among those individuals with the highest baseline autoimmunity (FIG. 2; patients 1, 4, and 6).

The protein array system that the inventors have developed for autoantibody screening can be used to assess antibodies against any antigen. To date, the inventors have developed an extended autoantibody profile that includes 18 nuclear antigens, 23 cytosolic/matrix antigens, 35 tissue-/organ-specific antigens, 43 cancer-specific antigens, and 18 pathogen-specific antigens. These panels have been regularly updated, and are therefore relatively exhaustive. However, depending on specific clinical context and questions, additional antigens can be validated and added.

The inventors' prior studies in thousands of patients with autoimmune diseases and normal controls position them to apply these technologies to oncology populations treated with immune checkpoint inhibitors. In addition to developing dynamic antigen panels, the inventors have developed processes for imputation of HLA genotypes using the Immunochip V2 platform and for determination of HLA regulatory elements (Raj et al., 2016), as well as T-cell and B-cell receptor sequencing (FIG. 3). Accordingly, these biomarkers are primed for clinical validation because we have already established accuracy, precision, analytical sensitivity and specificity, the reportable result range, reference intervals, reproducibility, and quality control in other populations (individuals with autoimmune disease and healthy controls). Similarly, the inventors' prior cross-trial data analyses establish our abilities to integrate and analyze biomarker and clinical data.

TABLE 3

Clinical Trials and Associated Biospecimens

| Trial | Indication | Treatment | N | Time-points | Status | Accrual (as of Jun. 17, 2016) |
|---|---|---|---|---|---|---|
| E4412 | Hodgkin's | Ipi. Nivo, Bren | 70 | Baseline, early, late | Activated January 2014 | 32 |
| EA5142 | NSCLC | Nivo | 714 | Baseline, recurrence | Activated May 2016 | 0 |

TABLE 4

Sample Size Estimation per Group for Evaluating Prediction Performance

| | | Alternative AUC | | | | |
|---|---|---|---|---|---|---|
| | | 0.65 | 0.7 | 0.75 | 0.8 | 0.85 |
| Null AUC | 0.5 | 115 | 64 | 40 | 28 | 20 |
| | 0.55 | 255 | 112 | 62 | 39 | 27 |
| | 0.6 | 987 | 244 | 107 | 59 | 37 |
| | 0.65 | — | 921 | 226 | 99 | 54 |

Null AUC refers to the Area Under Curve for each ROC under the null hypothesis, which represents the clinically meaningful prediction performance. Alternative AUC refers to AUC under alternative hypothesis, which represents the expected prediction performance for the new assays.

Example 2

Figure 4:
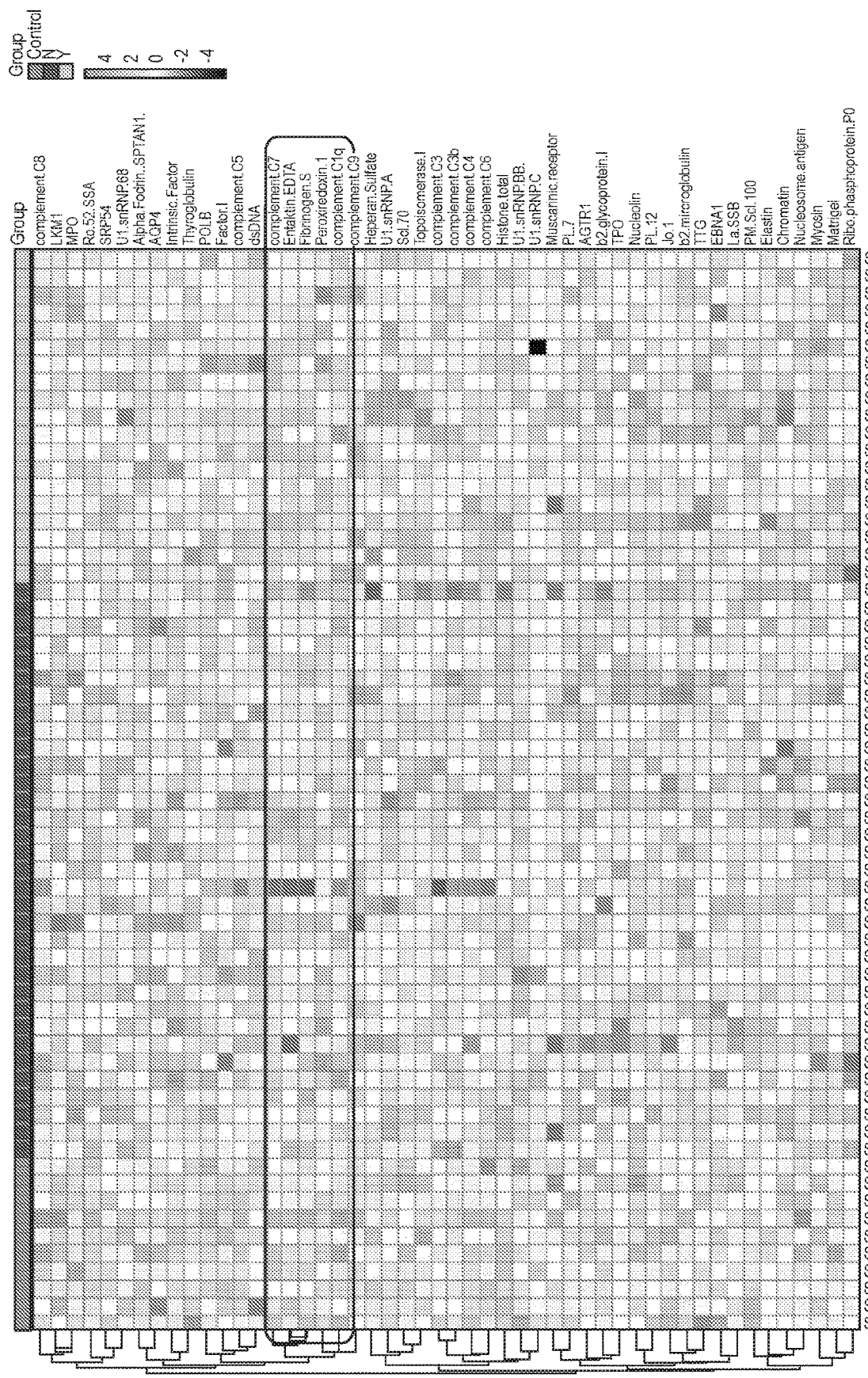

FIG. 4 shows assessment of 50 auto-antibodies in healthy controls, patients without AE and patient with AE. A stringent cutoff was used to only retain auto-antibodies with SNR>3 in all samples. As can be seen, auto-antibodies in the marked rectangle seem to be higher in patients who developed toxicity.

FIG. 5 is an ANOVA test that identified auto-antibodies with significant changes. Patients with AE show significantly elevated levels of complement protein C7, entaktin EDTA and fibrinogen S. It is notable that the fibrinogen, a blood coagulation protein, promotes autoimmunity and demyelination via chemokine release and antigen presentation, and autoimmune response again fibrinogen mediates inflammatory arthritis in mice. Moreover, anti-entaktin antibodies appear in patients with systemic lupus erythematosus and related disorders.

FIGS. 6-7 present data from the current patient cohort on four different self-antigens for which patients who developed irAes had statistically significant increases in the amounts of autoantibodies produced. These results are representative of the results obtained for the analysis of autoantibodies during immunoregulatory therapies. These antigens are correlating with toxicity in this patient cohort, which have predominantly undergone anti-PD1 or PDL1 therapies. Patients in other therapies, such as anti-CTLA4 therapy, may develop different antibodies. Similarly, patients developing autoimmune toxicity to specific organs, such as thyroid, bowel, lung, etc., are likely to develop target-specific antibodies. Thus, the panel of antigens that the inventors are utilizing is designed to allow simultaneous assessment of the potential for several autoimmune toxicities in patients at the outset and during immunotherapy.

FIGS. 8-9 show selection of IgG that may predict toxicity. Based on cross validation, baseline level of two IgG's can predict the toxicity at 65% accuracy, which, considering the toxicity rate is about 19/51 (37%). Entaktin and fibrinogen are consistently different between toxicity and non-toxicity groups both in multivariate and univariate analysis. As more patient are recruited, a higher prediction power may be achieved to permit testing of the prediction model in an independent testing set.

Table 5 presents the frequencies of autoantibodies binding a subset of the antigens from the arrays in cohorts of healthy normal individuals (NC), SLE patients, SSC patients, and IM patients. These data illustrate the frequencies of autoantibodies against individual antigens varies among the cohorts and that no single antigen is recognized by autoantibodies present in every patient with any of these diseases. Table 6 presents statistical data concerning the predictive value of detecting autoantibodies against each of these antigens for the three diseases. These data illustrate that although some of the autoantibodies are very predictive for a given antibody, none are uniquely present only in individuals with a given disease. Thus, the development of an effective assay to uniquely identify individuals with a specific disease with high sensitivity and specificity requires multivariant analysis with several antigens.

TABLE 5

IgG Autoantibody Score Data

| ID | Cut-off | NC (n = 330) | | SLE (n = 140) | | SSC (n = 72) | | IM (n = 74) | |
|---|---|---|---|---|---|---|---|---|---|
| | | No. +ve | +ve rate | No. +ve | +ve rate | No. +ve | +ve rate | No. +ve | +ve rate |
| Nucleosome | 11.9 | 6 | 1.8% | 121 | 86.4% | 26 | 36.1% | 19 | 25.7% |
| Sm | 13.8 | 12 | 3.6% | 110 | 78.6% | 3 | 4.2% | 1 | 1.4% |
| ssDNA | 12.5 | 10 | 3.0% | 100 | 71.4% | 11 | 15.3% | 5 | 6.8% |
| Ribo phaspho protein P | 12.3 | 5 | 1.5% | 95 | 67.9% | 17 | 23.6% | 14 | 18.9% |
| dsDNA | 14.5 | 10 | 3.0% | 89 | 63.6% | 2 | 2.8% | 1 | 1.4% |
| U1-snRNP-C | 15.7 | 5 | 1.5% | 86 | 61.4% | 14 | 19.4% | 8 | 10.8% |
| Chromatin | 13.9 | 2 | 0.6% | 86 | 61.4% | 2 | 2.8% | 1 | 1.4% |
| U1-snRNP-BB' | 7.8 | 6 | 1.8% | 85 | 60.7% | 16 | 22.2% | 3 | 4.1% |
| SmD | 11.0 | 7 | 2.1% | 77 | 55.0% | 7 | 9.7% | 3 | 4.1% |
| U1-snRNP-68 | 13.4 | 2 | 0.6% | 70 | 50.0% | 12 | 16.7% | 1 | 1.4% |
| dsRNA | 12.3 | 9 | 2.7% | 62 | 44.3% | 3 | 4.2% | 0 | 0.0% |
| KU -P70/P80 | 13.1 | 8 | 2.4% | 54 | 38.6% | 10 | 13.9% | 5 | 6.8% |
| Ro/SSA-60 KDa | 12.3 | 8 | 2.4% | 53 | 37.9% | 6 | 8.3% | 0 | 0.0% |
| Ribo phaspho protein P | 12.2 | 4 | 1.2% | 51 | 36.4% | 10 | 13.9% | 0 | 0.0% |
| CENP-B | 5.1 | 10 | 3.0% | 50 | 35.7% | 20 | 27.8% | 8 | 0.8% |
| U1-snRNP-A | 9.9 | 9 | 2.7% | 47 | 33.6% | 13 | 18.1% | 2 | 2.7% |
| Ribo phasphoprotein P | 13.2 | 3 | 0.9% | 47 | 33.6% | 4 | 5.6% | 1 | 1.4% |
| Ro/SSA-52 KDa | 11.9 | 10 | 3.0% | 46 | 32.9% | 10 | 13.9% | 24 | 32.4% |
| Scl-70 | 11.5 | 14 | 4.2% | 27 | 19.3% | 44 | 61.1% | 1 | 1.4% |
| Topoisomerase I | 14.3 | 13 | 3.9% | 17 | 12.1% | 40 | 55.6% | 1 | 1.4% |
| TTG | 11.3 | 4 | 1.2% | 9 | 6.4% | 34 | 47.2% | 13 | 17.6% |
| TPO | 13.3 | 10 | 3.0% | 15 | 10.7% | 28 | 38.9% | 1 | 1.4% |
| Cardolipin | 20.4 | 18 | 5.5% | 22 | 15.7% | 17 | 23.6% | 24 | 32.4% |
| Ro/SSA-52 KDa | 11.9 | 10 | 3.0% | 46 | 32.9% | 10 | 13.9% | 24 | 32.4% |
| Jo-1 | 27.6 | 13 | 3.9% | 13 | 9.3% | 4 | 5.6% | 24 | 32.4% |
| Mi-2 | 11.1 | 11 | 3.3% | 21 | 15.0% | 13 | 18.1% | 16 | 21.6% |
| PCNA | 18.7 | 8 | 2.4% | 28 | 20.0% | 4 | 5.6% | 14 | 18.9% |
| Collagen IV | 15.5 | 3 | 0.9% | 9 | 6.4% | 12 | 16.7% | 12 | 16.2% |
| LC1 | 12.6 | 12 | 3.6% | 36 | 25.7% | 6 | 8.3% | 12 | 16.2% |

TABLE 6

IgG Autoantibody Score Predictive Value

| | Predictive value for SLE | | | | Predictive value for SSC | | | | Predictive value for IM | | | |
| --- | --- | --- | --- | --- | --- | --- | --- | --- | --- | --- | --- | --- |
| ID | PPV | NPV | Sensitivity | Specificity | PPV | NPV | Sensitivity | Specificity | PPV | NPV | Sensitivity | Specificity |
| Nucleosome | 95.3% | 94.5% | 86.4% | 98.2% | 81.3% | 87.6% | 36.1% | 98.2% | 76.0% | #VALUE! | 25.7% | 98.2% |
| Sm | 90.2% | 91.4% | 78.6% | 96.4% | 20.0% | 82.2% | 4.2% | 96.4% | 7.7% | #VALUE! | 1.4% | 96.4% |
| ssDNA | 90.9% | 88.9% | 71.4% | 97.0% | 52.4% | 84.0% | 15.3% | 97.0% | 33.3% | #VALUE! | 6.8% | 97.0% |
| Ribo phaspho protein P1 | 95.0% | 87.8% | 67.9% | 98.5% | 77.3% | 85.5% | 23.6% | 98.5% | 73.7% | #VALUE! | 18.9% | 98.5% |
| dsDNA | 89.9% | 86.3% | 63.6% | 97.0% | 16.7% | 82.1% | 2.8% | 97.0% | 9.1% | #VALUE! | 1.4% | 97.0% |
| U1-snRNP-C | 94.5% | 85.8% | 61.4% | 98.5% | 73.7% | 84.9% | 19.4% | 98.5% | 61.5% | #VALUE! | 10.8% | 98.5% |
| Chromatin | 97.7% | 85.9% | 61.4% | 99.4% | 50.0% | 82.4% | 2.8% | 99.4% | 33.3% | #VALUE! | 1.4% | 99.4% |
| U1-snRNP-BB' | 93.4% | 85.5% | 60.7% | 98.2% | 72.7% | 85.3% | 22.2% | 98.2% | 33.3% | #VALUE! | 4.1% | 98.2% |
| SmD | 91.7% | 83.7% | 55.0% | 97.9% | 50.0% | 83.2% | 9.7% | 97.9% | 30.0% | #VALUE! | 4.1% | 97.9% |
| U1-snRNP-68 | 97.2% | 82.4% | 50.0% | 99.4% | 85.7% | 84.5% | 16.7% | 99.4% | 33.3% | #VALUE! | 1.4% | 99.4% |
| dsRNA | 87.3% | 80.5% | 44.3% | 97.3% | 25.0% | 82.3% | 4.2% | 97.3% | 0.0% | #VALUE! | 0.0% | 97.3% |
| KU-P70/P80 | 87.1% | 78.9% | 38.6% | 97.6% | 55.6% | 83.9% | 13.9% | 97.6% | 38.5% | #VALUE! | 6.8% | 97.6% |
| Ro/SSA-60 KDa | 86.9% | 78.7% | 37.9% | 97.6% | 42.9% | 83.0% | 8.3% | 97.6% | 0.0% | #VALUE! | 0.0% | 97.6% |
| Ribo phaspho protein P2 | 92.7% | 78.6% | 36.4% | 98.8% | 71.4% | 84.0% | 13.9% | 98.8% | 0.0% | #VALUE! | 0.0% | 98.8% |
| CENP-B | 83.3% | 78.0% | 35.7% | 97.0% | 66.7% | 86.0% | 27.8% | 97.0% | 44.4% | #VALUE! | 10.8% | 97.0% |
| U1-snRNP-A | 83.9% | 77.5% | 33.6% | 97.3% | 59.1% | 84.5% | 18.1% | 97.3% | 18.2% | #VALUE! | 2.7% | 97.3% |
| Ribo phaspho protein P0 | 94.0% | 77.9% | 33.6% | 99.1% | 57.1% | 82.8% | 5.6% | 99.1% | 25.0% | #VALUE! | 1.4% | 99.1% |
| Ro/SSA-52 KDa | 82.1% | 77.3% | 32.9% | 97.0% | 50.0% | 83.8% | 13.9% | 97.0% | 70.6% | #VALUE! | 32.4% | 97.0% |
| Scl-70 | 65.9% | 73.7% | 19.3% | 95.8% | 75.9% | 91.9% | 61.1% | 95.8% | 6.7% | #VALUE! | 1.4% | 95.8% |
| Topoisomerase I | 56.7% | 72.0% | 12.1% | 96.1% | 75.5% | 90.8% | 55.6% | 96.1% | 7.1% | #VALUE! | 1.4% | 96.1% |
| TTG | 69.2% | 71.3% | 6.4% | 98.8% | 89.5% | 89.6% | 47.2% | 98.8% | 76.5% | #VALUE! | 17.6% | 98.8% |
| TPO | 60.0% | 71.9% | 10.7% | 97.0% | 73.7% | 87.9% | 38.9% | 97.0% | 9.1% | #VALUE! | 1.4% | 97.0% |
| Cardolipin | 55.0% | 72.6% | 15.7% | 94.5% | 48.6% | 85.0% | 23.6% | 94.5% | 57.1% | 81.3% | 32.4% | 94.5% |
| Ro/SSA-52 KDa | 82.1% | 77.3% | 32.9% | 97.0% | 50.0% | 83.8% | 13.9% | 97.0% | 70.6% | 81.6% | 32.4% | 97.0% |
| Jo-1 | 50.0% | 71.4% | 9.3% | 96.1% | 23.5% | 82.3% | 5.6% | 96.1% | 64.9% | 81.9% | 32.4% | 96.1% |
| Mi-2 | 65.6% | 72.8% | 15.0% | 96.7% | 54.2% | 84.4% | 18.1% | 96.7% | 59.3% | 81.5% | 21.6% | 96.7% |
| PCNA | 77.8% | 74.2% | 20.0% | 97.6% | 33.3% | 82.6% | 5.6% | 97.6% | 63.6% | 81.9% | 18.9% | 97.6% |
| Collagen IV | 75.0% | 71.4% | 6.4% | 99.1% | 80.0% | 84.5% | 16.7% | 99.1% | 80.0% | 81.5% | 16.2% | 99.1% |
| LC1 | 75.0% | 75.4% | 25.7% | 96.4% | 33.3% | 82.8% | 8.3% | 96.4% | 50.0% | 81.8% | 16.2% | 96.4% |

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VI. REFERENCES

The following references, to the extent that they provide exemplary procedural or other details supplementary to those set forth herein, are specifically incorporated herein by reference.

"Antibodies: A Laboratory Manual," Cold Spring Harbor Press, Cold Spring Harbor, NY, 1988.
Abbondanzo et al., Am. J. Pediatr. Hematol. Oncol., 12(4), 480-489, 1990.
Allred et al., Arch. Surg., 125(1), 107-113, 1990.
Brown et al., J. Immunol. Meth., 12; 130(1): 111-121, 1990.
Campbell, In: Monoclonal Antibody Technology, Laboratory Techniques in Biochemistry and Molecular Biology, Vol. 13, Burden and Von Knippenberg, Eds. pp. 75-83, Amsterdam, Elsevier, 1984.
De Jager et al., Semin. Nucl. Med. 23(2), 165-179, 1993.
Doolittle and Ben-Zeev, Methods Mol. Biol., 109, 215-237, 1999.
Gulbis and Galand, Hum. Pathol. 24(12), 1271-1285, 1993.
Nakamura et al., In: Enzyme Immunoassays: Heterogeneous and Homogeneous Systems, Chapter 27, 1987.
Remington's Pharmaceutical Sciences, 15th Ed., 3:624-652, 1990.
U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
Hamanishi et al., J Clin Oncol 33; 4015-22, 2015.
Ansell et al., N Engl J Med 372:311-9, 2015.
McDermott et al., J Clin Oncol 33:2013-20, 2015.
Early Breast Cancer Trialists' Collaborative Group, Lancet 351:1451-67, 1998.
Le et al., N Engl J Med 372:2509-20, 2015.
Howell et al., Lung Cancer 88:117-23, 2015.
Postow et al., N Engl J Med 372:2006-17, 2015.
Wild, D. (ed.). "The Immunoassay Handbook," Waltham, MA, Elsevier; Chapter 9.15, 2013.
Khan et al., JAMA Oncology 2:1507-8, 2016.
Topalian et al., N Engl J Med 366:2443-54, 2012.
Horvat et al., J Clin Oncol 33:3193-8, 2015.
Allison et al., Eur J Immunol 28:949-60, 1998a.
Gubin et al., Nature 515:577-81, 2014.
Allison et al., Novartis Found Symp 215:92-8; discussion 98-102, 186-90, 1998b
Cooper et al., J Autoimmun 33:197-207, 2009.
Khan et al., JAMA Oncol, 2016 Jun. 4. Epub ahead of print.
Wandstrat et al., J Autoimmun 27:153-60, 2006.

Li et al., *Arthritis Res Ther* 13:R38, 2011.
Li and Wakeland, *Genomics Proteomics Bioinformatics* 13:205-7, 2015.
Tan et al., *Arthritis Rheum* 40:1601-11, 1997.
Kristiansen et al., *Genes Immun* 1:170-84, 2000.
Romo-Tena et al., *Autoimmun Rev* 12:1171-6, 2013.
Gianchecchi et al., *Autoimmun Rev* 12:1091-100, 2013.
Raj et al., *Elife* 5, 2016.

What is claimed is:

1. A method of treating a human subject with cancer to mitigate or prevent cancer immunotherapy toxicity comprising:
    (a) providing an antibody-containing sample from said subject wherein the sample is obtained prior to treatment with cancer immunotherapy;
    (b) assessing two or more autoantibody levels in said sample, wherein the two or more autoantibody levels comprise entaktin autoantibody level and fibrinogen autoantibody level; and
    (c) treating said subject with:
        (i) a cancer immunotherapy when said autoantibody levels are below populational average;
        (ii) a non-immunotherapy cancer treatment when said autoantibody levels are above populational average; or
        (iii) a cancer immunotherapy and a toxicity mitigating therapy when said autoantibody levels are above populational average,
    wherein treating said subject mitigates or prevents cancer immunotherapy toxicity in said subject.

2. The method of claim 1, wherein the sample is a whole blood, serum, plasma, or other body fluid.

3. The method of claim 1, wherein the assessing two or more autoantibody levels in said sample, further comprises assessing autoantibody levels to:
    (a) two or more antigens, wherein the two or more antigens comprise: A100, Aggrecan, AGTR, Alpha Fodrin (SPTAN1), alpha-actinin, Amyloid, AQP4 recombinant, BPI, Cardolipin, CENP-A, CENP-B, Chondroitin Sulfate C, Chromatin, Collagen I, Collagen II, Collagen III, Collagen IV, Collagen V, Collagen VI, complement C1q, complement C3, complement C3a, complement C3b, complement C4, complement C5, complement C6, complement C7, complement C8, complement C9, CRP antigen, Cytochrome C, Decorin-bovine, DGPS, dsDNA, EBNA1, Elastin, Entaktin EDTA, Factor I, Factor P, FactorB, FactorD, FactorH, Fibrinogen IV, Fibrinogen S, Fibronectin, GBM (disso), Gliadin (IgG), Glycated Albumin, GP2, gP210, H1, H2A, H2B, H3, H4, Hemocyanin, Heparan HSPG, Heparin, Heperan Sulfate, Histone-total, human genomic DNA, Intrinsic Factor, Jo-1, KU (P70/P80), La/SSB, Laminin, LC1, LKM1, M2 Antigen, Matrigel, MDAS, Mi-2, Mitochondrial antigen, MPO, Muscarinic receptor, Myelin basic protein (MBP), Myelin-associated glycoprotein-FC (MAG), Myosin, Nucleolin, Nucleosome antigen, Nup62, PCNA, Peroxiredoxin 1, Phophatidylinositol, PL-12, PL-7, PM/Scl-100, PM/Scl-75, POLB, PR3, Proteoglycan, Prothrombin protein, Ribo phospho protein P1, Ribo phospho protein P2, Ribo phosphoprotein P0, Ro/SSA (52 KDa), Ro/SSA (60 KDa), Scl-70, Sm, Sm/RNP, SmD, SmD1, SmD2, SmD3, SP100, Sphingomyelin, SRP54, ssDNA, ssRNA, T1F1 GAMMA, Thyroglobulin, TNFa, Topoisomerase I, TPO, TTG, U1-snRNP-68, U1-snRNP-A, U1-snRNP-BB', U1-snRNP-C, Vimentin, Vitronectin, β2-glycoprotein I, β2-microglobulin, IgG Control, and anti-Ig,
    (b) two or more antigens, wherein the two or more antigens are selected from: A100, Aggrecan, AGTR, Alpha Fodrin (SPTAN1), alpha-actinin, Amyloid, AQP4 recombinant, BPI, Cardolipin, CENP-A, CENP-B, Chondroitin Sulfate C, Chromatin, Collagen I, Collagen II, Collagen III, Collagen IV, Collagen V, Collagen VI, complement C1a, complement C3, complement C3a, complement C3b, complement C4, complement C5, complement C6, complement C7, complement C8, complement C9, CRP antigen, Cytochrome C, Decorin-bovine, DGPS, dsDNA, EBNA1, Elastin, Entaktin EDTA, Factor I, Factor P, FactorB, FactorD, FactorH, Fibrinogen IV, Fibrinogen S, Fibronectin, GBM (disso), Gliadin (IgG), Glycated Albumin, GP2, qP210, H1, H2A, H2B, H3, H4, Hemocyanin, Heparan HSPG, Heparin, Heperan Sulfate, Histone-total, human genomic DNA, Intrinsic Factor, Jo-1, KU (P70/P80), La/SSB, Laminin, LC1, LKM1, M2 Antigen, Matrigel, MDAS, Mi-2, Mitochondrial antigen, MPO, Muscarinic receptor, Myelin basic protein (MBP), Myelin-associated glycoprotein-FC (MAG), Myosin, Nucleolin, Nucleosome antigen, Nup62, PCNA, Peroxiredoxin 1, Phophatidylinositol, PL-12, PL-7, PM/Scl-100, PM/Scl-75, POLB, PR3, Proteoglycan, Prothrombin protein, Ribo phospho protein P1, Ribo phospho protein P2, Ribo phosphoprotein P0, Ro/SSA (52 KDa), Ro/SSA (60 KDa), Scl-70, Sm, Sm/RNP, SmD, SmD1, SmD2, SmD3, SP100, Sphingomyelin, SRP54, ssDNA, ssRNA, T1F1 GAMMA, Thyroglobulin, TNFa, Topoisomerase I, TPO, TTG, U1-snRNP-68, U1-snRNP-A, U1-snRNP-BB', U1-snRNP-C, Vimentin, Vitronectin, β2-glycoprotein I, β2-microglobulin, IgG Control, anti-Ig, CMV-G, CMV-M, CMV EXT-2, CMV GRADE III, HEPATITIS A, HAV CONCENTRATE, HSV-1, HSV-2, RUBEOLA, RSV, ROTAVIRUS SA-11, RUBELLA VIRUS GRADE III, RUBELLA VIRUS GRADE IV, RUBELLA GRADE IV, RSVP, *TOXOPLASMA* Antigen, VZV, VZV GRADE II, HUMAN AZUROCDIN, House Dust, Dog Dander, Dog Epithelia, Beef *Bos taurus*, Shrimp Penacidae, Peanut *Arachis hypogaea*, Wheat Whole *Triticum aestivum*, Mite House Dust *Blomia tropicalis*, Bermuda *Cynodon dactylon*, Cedar Red Juniper rus *virginiana*, Plantain English *Plantago lanceolata*, Honey Bee *Apis mellifera*, 3-hydroxy-3-methylglutaryl-coenzyme A reductase, Aminoacyl-tRNA Synthetase, Asparaginyl-tRNA Synthetase(KS), Glycyl-tRNA Synthetase(EJ), Lysyl-tRNA Synthetase, Phenylalanyl-tRNA Synthetase 2, Human Cytosolic 5'-nucleotidase 1A, glutaminyl-tRNA Synthetase, MORC family CW-type zinc finger 3 (MORC3), signal recognition particle 14 kDa, SUMO1 activating enzyme subunit 1(SAE1), tryptophanyl-tRNA Synthetase(WARS), tyrosyl-tRNA Synthetase(YARS), ubiquitin-like modifier activating anzyme 2(UBA2), NY-ESO-1, Prostatic Acid Phosphatase, Prostate Specific Membrane Antigen, MAGEA3, FOLH1, PSA, CA 125, CEA, PSMA/FOLH1/NAALADase 1, Myosin Light Chain, Muscarinic receptor, Albumin Bovine fraction V, AQP4, DNA Polymerase beta Protein, EBV EBNA1, AGTR1(angiotension receptor1), Collagenase A, Collagenase D, Tetanus toxin, or any combination thereof, (c) two or more antigens wherein the two or more antigens comprise: A100, Aggrecan, AGTR, Alpha Fodrin (SPTAN1), alpha-actinin, Amyloid, AQP4 recombinant, BPI, Cardolipin, CENP-A, CENP-B, Chondroitin Sulfate C, Chromatin, Collagen I, Collagen II, Collagen III, Collagen IV, Collagen V, Collagen VI, complement C1q, complement C3, complement C3a, complement C3b, complement C4, complement C5, complement C6, complement C7, complement C8, complement C9, CRP antigen, Cytochrome C, Decorin-bovine, DGPS, dsDNA, EBNA1, Elastin, Entaktin EDTA, Factor I, Factor P, FactorB, FactorD, FactorH, Fibrinogen IV, Fibrinogen S, Fibronectin, GBM (disso), Gliadin (IgG), Glycated Albumin, GP2, gP210, H1, H2A, H2B, H3, H4, Hemocyanin, Heparan HSPG, Heparin, Heperan Sulfate, Histone-total, human genomic DNA, Intrinsic Factor, Jo-1, KU (P70/P80), La/SSB, Laminin, LC1, LKM1, M2 Antigen, Matrigel, MDA5, Mi-2, Mitochondrial antigen, MPO, Muscarinic receptor, Myelin basic protein (MBP), Myelin-associated glycoprotein-FC (MAG), Myosin, Nucleolin, Nucleosome antigen, Nup62, PCNA, Peroxiredoxin 1, Phophatidylinositol, PL-12, PL-7, PM/Scl-100, PM/Scl-75, POLB, PR3, Proteoglycan, Prothrombin protein, Ribo phaspho protein P1, Ribo phaspho protein P2, Ribo phasphoprotein P0, Ro/SSA (52 KDa), Ro/SSA (60 KDa), Scl-70, Sm, Sm/RNP, SmD, SmD1, SmD2, SmD3, SP100, Sphingomyelin, SRP54, ssDNA, ssRNA, T1F1 GAMMA, Thyroglobulin, TNFa, Topoisomerase I, TPO, TTG, U1-snRNP-68, U1-snRNP-A, U1-snRNP-BB', U1-snRNP-C, Vimentin, Vitronectin, 82-glycoprotein I, 82-microglobulin, IgG Control, and anti-Ig, and two or more antigens selected from CMV-G, CMV-M, CMV EXT-2, CMV GRADE III, HEPATITIS A, HAV CONCENTRATE, HSV-1, HSV-2, RUBEOLA, RSV, ROTAVIRUS SA-11, RUBELLA VIRUS GRADE III, RUBELLA VIRUS GRADE IV, RUBELLA GRADE IV, RSVP, *TOXOPLASMA* Antigen, VZV, VZV GRADE II, HUMAN AZUROCDIN, House Dust, Dog Dander, Dog Epithelia, Beef *Bos taurus*, Shrimp Penacidae, Peanut *Arachis hypogaea*, Wheat Whole *Triticum aestivum*, Mite House Dust *Blomia tropicalis*, Bermuda *Cynodon dactylon*, Cedar Red Juniper rus virginiana, Plantain English *Plantago lanceolata*, Honey Bee *Apis mellifera*, 3-hydroxy-3-methylglutaryl-coenzyme A reductase, Aminoacyl-tRNA Synthetase, Asparaginyl-tRNA Synthetase(KS), Glycyl-tRNA Synthetase(EJ), Lysyl-tRNA Synthetase, Phenylalanyl-tRNA Synthetase 2, Human Cytosolic 5'-nucleotidase 1A, glutaminyl-tRNA Synthetase, MORC family CW-type zinc finger 3 (MORC3), signal recognition particle 14 kDa, SUMO1 activating enzyme subunit 1(SAE1), tryptophanyl-tRNA Synthetase(WARS), tyrosyl-tRNA Synthetase(YARS), ubiquitin-like modifier activating anzyme 2(UBA2), NY-ESO-1, Prostatic Acid Phosphatase, Prostate Specific Membrane Antigen, MAGEA3, FOLH1, PSA, CA 125, CEA, PSMA/FOLH1/NAALADase 1, Myosin Light Chain, Muscarinic receptor, Albumin Bovine fraction V, AQP4, DNA Polymerase beta Protein, EBV EBNA1, AGTR1(angiotension receptor1), Collagenase A, Collagenase D, Tetanus toxin, Ig Control, Anti-Ig, or any combination thereof, or (d) two or more antigens wherein the two or more antigens comprise: A100, Aggrecan, AGTR, Alpha Fodrin (SPTAN1), alpha-actinin, Amyloid, AQP4 recombinant, BPI, Cardolipin, CENP-A, CENP-B, Chondroitin Sulfate C, Chromatin, Collagen I, Collagen II, Collagen III, Collagen IV, Collagen V, Collagen VI, complement C1q, complement C3, complement C3a, complement C3b, complement C4, complement C5, complement C6, complement C7, complement C8, complement C9, CRP antigen, Cytochrome C, Decorin-bovine, DGPS, dsDNA, EBNA1, Elastin, Entaktin EDTA, Factor I, Factor P, FactorB, FactorD, FactorH, Fibrinogen IV, Fibrinogen S, Fibronectin, GBM (disso), Gliadin (IgG), Glycated Albumin, GP2, gP210, H1, H2A, H2B, H3, H4, Hemocyanin, Heparan HSPG, Heparin, Heperan Sulfate, Histone-total, human genomic DNA, Intrinsic Factor, Jo-1, KU (P70/P80), La/SSB, Laminin, LC1, LKM1, M2 Antigen, Matrigel, MDA5, Mi-2, Mitochondrial antigen, MPO, Muscarinic receptor, Myelin basic protein (MBP), Myelin-associated glycoprotein-FC (MAG), Myosin, Nucleolin, Nucleosome antigen, Nup62, PCNA, Peroxiredoxin 1, Phophatidylinositol, PL-12, PL-7, PM/Scl-100, PM/Scl-75, POLB, PR3, Proteoglycan, Prothrombin protein, Ribo phaspho protein P1, Ribo phaspho protein P2, Ribo phasphoprotein P0, Ro/SSA (52 KDa), Ro/SSA (60 KDa), Scl-70, Sm, Sm/RNP, SmD, SmD1, SmD2, SmD3, SP100, Sphingomyelin, SRP54, ssDNA, ssRNA, T1F1 GAMMA, Thyroglobulin, TNFa, Topoisomerase I, TPO, TTG, U1-snRNP-68, U1-snRNP-A, U1-snRNP-BB', U1-snRNP-C, Vimentin, Vitronectin, 82-glycoprotein I, 82-microglobulin, IgG Control, and anti-Ig, CMV-G, CMV-M, CMV EXT-2, CMV GRADE III, HEPATITIS A, HAV CONCENTRATE, HSV-1, HSV-2, RUBEOLA, RSV, ROTAVIRUS SA-11, RUBELLA VIRUS GRADE III, RUBELLA VIRUS GRADE IV, RUBELLA GRADE IV, RSVP, *TOXOPLASMA* Antigen, VZV, VZV GRADE II, HUMAN AZUROCDIN, House Dust, Dog Dander, Dog Epithelia, Beef *Bos taurus*, Shrimp Penacidae, Peanut *Arachis hypogaea*, Wheat Whole *Triticum aestivum*, Mite House Dust *Blomia tropicalis*, Bermuda *Cynodon dactylon*, Cedar Red Juniper rus virginiana, Plantain English *Plantago lanceolata*, Honey Bee *Apis mellifera*, 3-hydroxy-3-methylglutaryl-coenzyme A reductase, Aminoacyl-tRNA Synthetase, Asparaginyl-tRNA Synthetase(KS), Glycyl-tRNA Synthetase(EJ), Lysyl-tRNA Synthetase, Phenylalanyl-tRNA Synthetase 2, Human Cytosolic 5'-nucleotidase 1A, glutaminyl-tRNA Synthetase, MORC family CW-type zinc finger 3 (MORC3), signal recognition particle 14 kDa, SUMO1 activating enzyme subunit 1(SAE1), tryptophanyl-tRNA Synthetase(WARS), tyrosyl-tRNA Synthetase(YARS), ubiquitin-like modifier activating anzyme 2(UBA2), NY-ESO-1, Prostatic Acid Phosphatase, Prostate Specific Membrane Antigen, MAGEA3, FOLH1, PSA, CA 125, CEA, PSMA/FOLH1/NAALADase 1, Myosin Light Chain, Muscarinic receptor, Albumin Bovine fraction V, AQP4, DNA Polymerase beta Protein, EBV EBNA1, AGTR1(angiotension receptor1), Collagenase A, Collagenase D, and Tetanus toxin.

4. The method of claim 1, wherein assessing comprises ELISA, RIA, Western blot, fluorescence-based antibody screening protein microarray, bead array, cartridges, lateral flow, or line-probe assays.

5. The method of claim 1, further comprising (d) assessing therapeutic toxicity, wherein the assessing therapeutic toxicity comprises:

(i) providing an antibody-containing sample from said subject wherein the sample is obtained at a time point after step (c);

(ii) assessing two or more autoantibody levels in said sample, wherein the two or more autoantibody levels comprise entaktin autoantibody level and fibrinogen autoantibody level, thereby permitting assessment of therapeutic toxicity.

6. The method of claim 1, further comprising performing a control reaction with known autoantibody standards.

7. The method of claim 1, wherein said immunotherapy comprises administration of an immune checkpoint inhibitor, a chimeric antigen receptor, or an immunotoxin.

8. The method of claim 1, wherein said immunotherapy comprises administration of an anti-CTLA4 antibody, an anti-PD1 antibody, or an anti-PD1 ligand.

9. The method of claim 1, wherein said immunotherapy comprises a combination of multiple immunotherapeutic agents or a combination of an immunotherapeutic agent and a non-immunotherapeutic agent.

10. The method of claim 1, wherein said subject has previously been diagnosed with an autoimmune disease.

11. The method of claim 1, wherein said subject has not previously been diagnosed with an autoimmune disease.

12. The method of claim 1, wherein said subject has lung cancer, melanoma, head & neck cancer, kidney cancer, or lymphoma, or bladder cancer.

13. The method of claim 1, further comprising assessing a rate of increase or decrease in autoantibody level.

14. The method of claim 1, further comprising classifying immunotherapy toxicity based on organ or organ system in said subject.

15. The method of claim 14, wherein said organ or organ system is skin, lung, central/peripheral nervous system, pituitary gland, eye, heart, gastrointestinal tract, thyroid, adrenal gland, liver, pancreas, or kidney.

16. The method of claim 1, wherein said subject is further characterized as receiving a molecular targeted therapy, a chemotherapy, a chemoembolization, a radiotherapy, a radiofrequency ablation, a hormone therapy, a bland embolization, a surgery, or a second distinct immunotherapy.

17. The method of claim 1, wherein the toxicity mitigating therapy is a corticosteroids a TNF inhibitor, or hormone replacement.

* * * * *